(12) United States Patent
Watanabe et al.

(10) Patent No.: US 8,431,401 B2
(45) Date of Patent: Apr. 30, 2013

(54) METHOD OF CULTIVATING CELL OR TISSUE

(75) Inventors: Setsuo Watanabe, Fuji (JP); Shuichi Mizuno, Brookline, MA (US)

(73) Assignee: Takagi Industrial Co., Ltd., Fuji-shi, Shizuoka (JP)

( * ) Notice: Subject to any disclaimer, the term of this patent is extended or adjusted under 35 U.S.C. 154(b) by 397 days.

(21) Appl. No.: 12/307,978

(22) PCT Filed: Jun. 22, 2007

(86) PCT No.: PCT/JP2007/062587
§ 371 (c)(1),
(2), (4) Date: Jan. 8, 2009

(87) PCT Pub. No.: WO2008/007527
PCT Pub. Date: Jan. 17, 2008

(65) Prior Publication Data
US 2009/0298181 A1   Dec. 3, 2009

(30) Foreign Application Priority Data

Jul. 10, 2006   (JP) ................. 2006-189732

(51) Int. Cl.
  *C12N 5/00*   (2006.01)
(52) U.S. Cl.
  USPC .......................... 435/395; 435/401
(58) Field of Classification Search .......... 435/395, 435/401
  See application file for complete search history.

(56) References Cited

U.S. PATENT DOCUMENTS

| | | | |
|---|---|---|---|
| 4,456,683 A | | 6/1984 | Lintilhac et al. |
| 5,217,889 A | | 6/1993 | Roninson et al. |
| 5,406,853 A | * | 4/1995 | Lintilhac et al. ............... 73/789 |
| 5,452,236 A | | 9/1995 | Lintilhac et al. |
| 5,736,399 A | | 4/1998 | Takezawa et al. |
| 6,242,247 B1 | | 6/2001 | Rieser et al. |
| 6,387,693 B2 | | 5/2002 | Rieser et al. |
| 6,432,713 B2 | | 8/2002 | Takagi et al. |
| 7,541,178 B2 | | 6/2009 | Takagi et al. |
| 7,547,540 B2 | * | 6/2009 | Takagi et al. ............... 435/289.1 |
| 7,585,323 B2 | * | 9/2009 | Masini et al. ............... 623/16.11 |
| 7,807,453 B2 | * | 10/2010 | Quinn et al. ............... 435/289.1 |
| 7,906,323 B2 | | 3/2011 | Cannon et al. |
| 2001/0014473 A1 | | 8/2001 | Rieser et al. |
| 2001/0021529 A1 | | 9/2001 | Takagi |
| 2001/0043918 A1 | | 11/2001 | Masini et al. |
| 2002/0037586 A1 | * | 3/2002 | Takagi et al. ............... 435/395 |
| 2003/0199083 A1 | | 10/2003 | Vilendrer et al. |
| 2004/0077072 A1 | | 4/2004 | Takagi et al. |
| 2004/0235153 A1 | | 11/2004 | Takagi et al. |
| 2005/0048643 A1 | * | 3/2005 | Takagi et al. ............... 435/289.1 |
| 2005/0106716 A1 | | 5/2005 | Takagi et al. |
| 2006/0147486 A1 | | 7/2006 | Kim et al. |
| 2006/0270023 A1 | | 11/2006 | LeDuc et al. |

FOREIGN PATENT DOCUMENTS

| | | |
|---|---|---|
| CA | 2543374 A1 | 5/2005 |
| CN | 1427888 | 7/2003 |
| CN | 1737106 | 2/2006 |
| CN | 1737107 | 2/2006 |
| CN | 1898375 A | 1/2007 |
| CN | 100354406 | 12/2007 |
| EP | 0112590 A2 | 7/1984 |
| EP | 126696 | 11/1984 |
| EP | 0441639 A1 | 8/1991 |
| EP | 0671469 | 9/1995 |
| EP | 0671469 A2 | 9/1995 |
| EP | 0922093 | 6/1999 |
| EP | 1382670 | 1/2004 |
| EP | 1428869 | 6/2004 |
| EP | 1464696 | 10/2004 |
| JP | 3163533 B2 | 7/1991 |
| JP | 05007487 A | 1/1993 |
| JP | 07298876 | 11/1995 |
| JP | 07298876 A | 11/1995 |
| JP | 09313166 | 12/1997 |
| JP | 10-155475 A | 6/1998 |
| JP | 10155475 A | 6/1998 |
| JP | 11504216 A | 4/1999 |
| JP | 2000513214 A | 10/2000 |
| JP | 2001238663 | 9/2001 |
| JP | 2002315566 | 10/2002 |
| JP | 2003061642 | 3/2003 |

(Continued)

OTHER PUBLICATIONS

International Preliminary Report and Written Opinion of International Application No. PCT/JP2007/062587 dated Jan. 20, 2009.

(Continued)

*Primary Examiner* — Karen Cochrane Carlson
*Assistant Examiner* — Natalie Moss
(74) *Attorney, Agent, or Firm* — Novak Druce Connolly Bove + Quigg LLP

(57) ABSTRACT

A method for cultivating a culture of a cell, tissue, etc. There is provided a method of cultivating a culture including a cell or tissue (cell construct), imparting bending motion to the culture. By virtue of applying bending force to a culture of a cell, tissue, etc. (cell construct) to thereby curve the culture, continuous compression and extension in a direction of thickness from a concave portion toward a convex portion thereof are induced. The physical stimulation and deformation not attained by conventional pressurization, shear and tension, then can be loaded on the culture to thereby realize the culture appropriate for restoration of tissue at a region accompanied by bending.

14 Claims, 18 Drawing Sheets

FOREIGN PATENT DOCUMENTS

| | | |
|---|---|---|
| JP | 2003-169663 A | 6/2003 |
| JP | 2003180331 | 7/2003 |
| JP | 2004512031 A | 4/2004 |
| JP | 2005143343 A | 6/2005 |
| JP | 2006513013 A | 4/2006 |
| JP | 2008017717 | 1/2008 |
| WO | 9746665 | 12/1997 |
| WO | WO-0164848 | 9/2001 |
| WO | WO-0226116 | 4/2002 |
| WO | 03029398 A1 | 4/2003 |
| WO | WO-03054137 | 7/2003 |
| WO | WO-03/085101 A1 | 10/2003 |
| WO | WO-2004094586 A2 | 11/2004 |
| WO | WO-2006015304 A2 | 2/2006 |
| WO | WO-2008007525 | 1/2008 |

OTHER PUBLICATIONS

"Mechanical Stimulation Improves Tissue-Engineered Human Skeletal Muscle," by Courtney A. Powell, et al.; Am J Physiol Cell Physiol 283: C1557-C1565, 2002, first published Jul. 17, 2002.

Canadian Office Action issued in related Canadian Patent Application No. 2,658,235 on Jul. 27, 2010.

Brown, T., "Techniques for mechanical stimulation of cells in vitro: a review." *Journal of Biomechanics* 33 (2000), 3-14.

Office Action of Jan. 8, 2009 in corresponding U.S. Appl. No. 12/307,986.

Office Action of Jan. 24, 2012 in JP patent application No. 2006-189732 (with English translation).

Office Action of Feb. 1, 2012 in corresponding U.S. Appl. No. 12/307,986.

Chinese Office Action of Apr. 25, 2011 in corresponding Chinese Patent Application No. 200780025260.2.

Chinese Office Action of Aug. 21, 2012 in corresponding Chinese Patent Application No. 200780025260.2.

Chinese Office Action of Jun. 9, 2011 in relevant Chinese Application No. 200780026057.7.

Office Action of Sep. 13, 2012 in relevant U.S. Appl. Serial No. 12/307,986.

Engelmayr., G.C., et al., *A novel bioreactor for the dynamic flexural stimulation of tissue engineered heart valve biomaterials* (2003), vol. 24, No. 14, pp. 2523-2532, Biomaterials, Elsevier Science Publishers.

Sodian, R., et al., *New Pulsatile Bioreactor for Fabrication of Tissue-Engineered Patches* (2001), vol. 8, No. 4, pp. 401-405, Journal of Biomedical Materials Research, Wiley.

Supplementary European Search Report for relevant EP Patent Application No. 07767247.5 issued Nov. 5, 2012.

Supplementary European Search Report for corresponding EP Patent Application No. 07767398.6 issued Nov. 5, 2012.

Japanese Office Action issued in corresponding Japanese Patent Application No. 2006-189732.

Chinese Office Action issued in relevant Chinese Patent Application No. 200780026057.7.

Sodian, R., et al., *New Pulsatile Bioreactor for Fabrication of Tissue-Engineered Patches* (2001), vol. 58, No. 4, pp. 401-405, Journal of Biomedical Materials Research, Wiley.

\* cited by examiner

FIG.7A
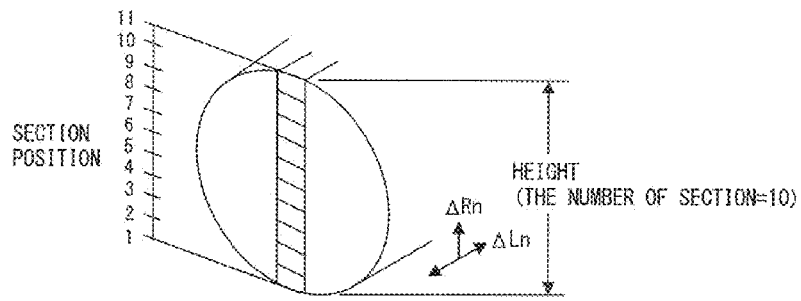
FIG.7B
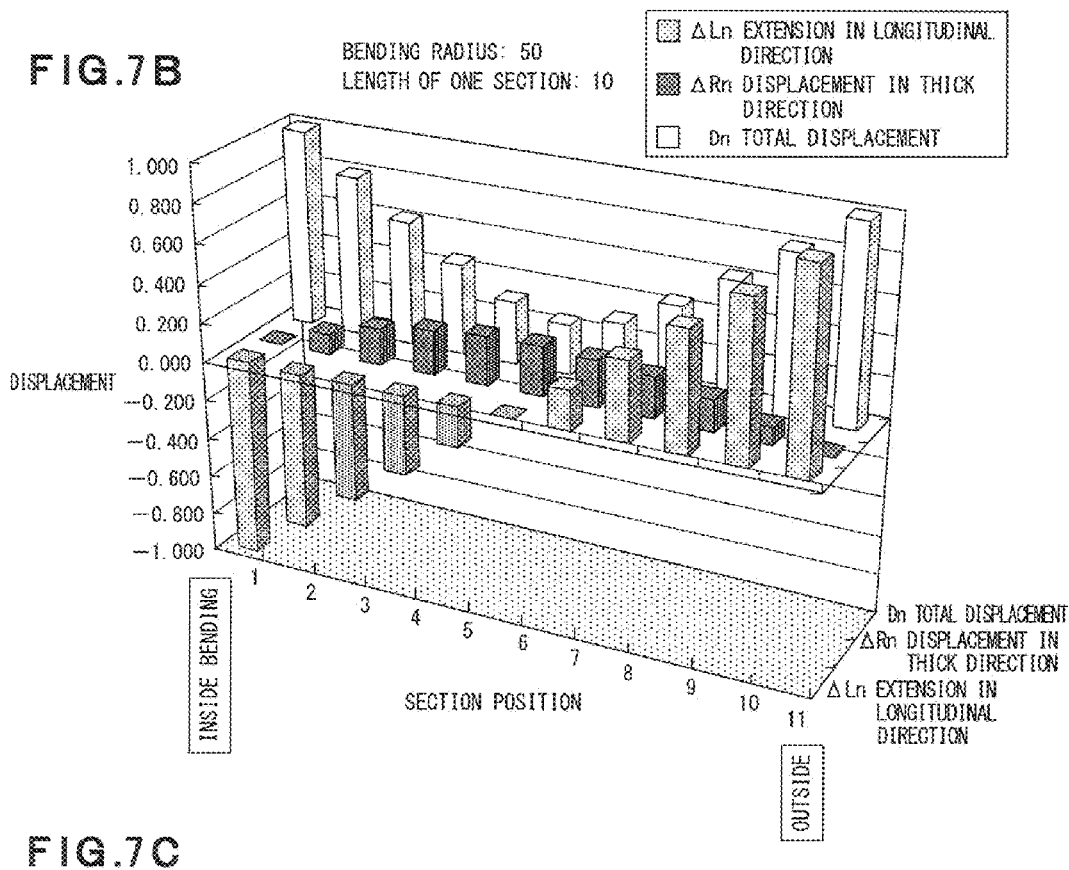
FIG.7C
|   | 1 | 2 | 3 | 4 | 5 | 6 | 7 | 8 | 9 | 10 | 11 |
|---|---|---|---|---|---|---|---|---|---|----|----|
| ΔLn | -1.000 | -0.800 | -0.600 | -0.400 | -0.200 | 0.000 | 0.200 | 0.400 | 0.600 | 0.800 | 1.000 |
| ΔRn | 0.000 | 0.098 | 0.170 | 0.218 | 0.244 | 0.249 | 0.235 | 0.202 | 0.151 | 0.083 | 0.000 |
| Dn | 1.000 | 0.806 | 0.624 | 0.456 | 0.316 | 0.249 | 0.308 | 0.448 | 0.619 | 0.804 | 1.000 |

FIG.8A
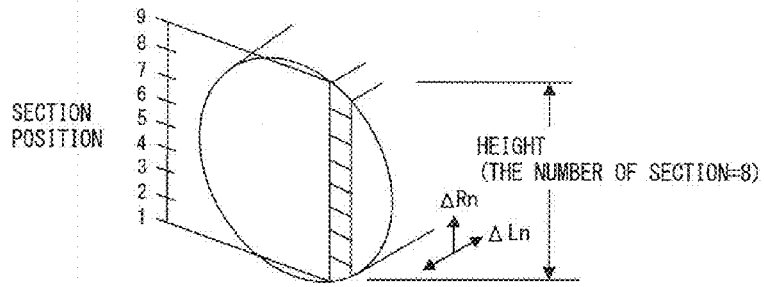
FIG.8B
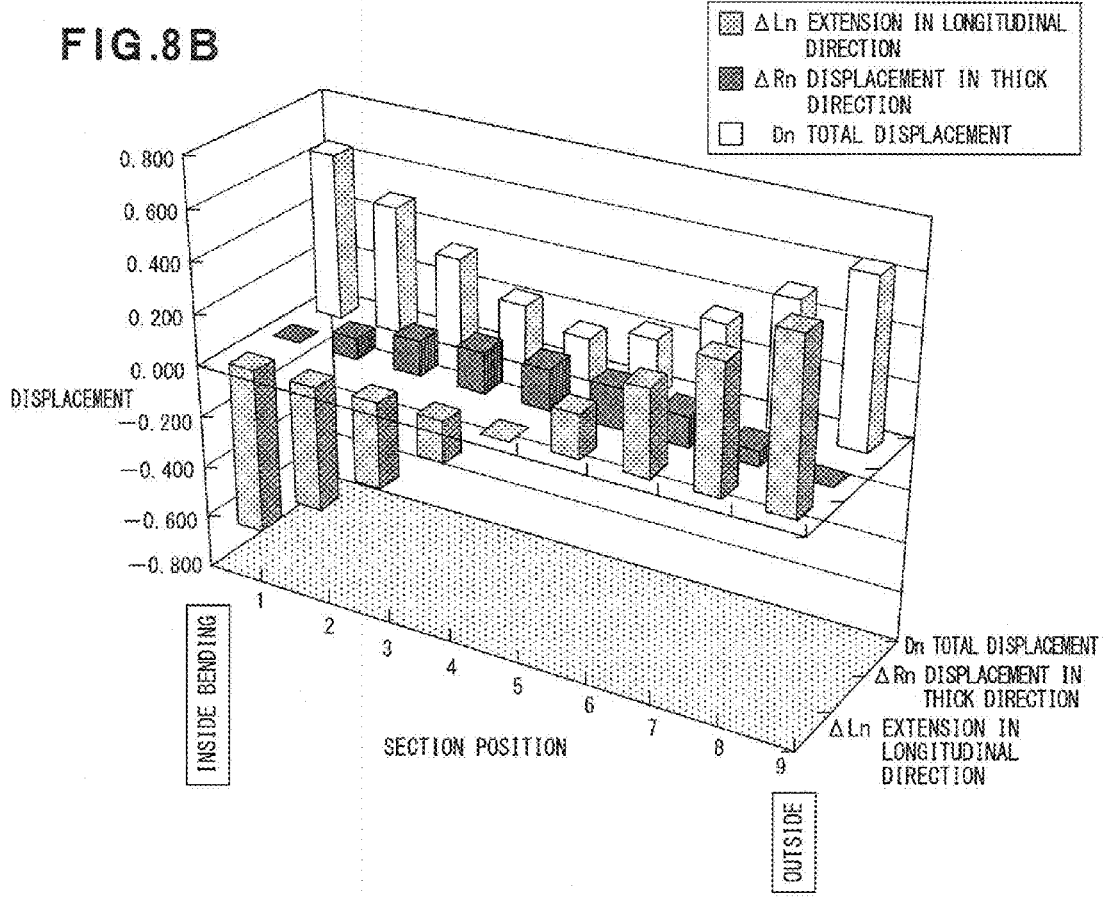
FIG.8C
|  | 1 | 2 | 3 | 4 | 5 | 6 | 7 | 8 | 9 |
|---|---|---|---|---|---|---|---|---|---|
| $\Delta Ln$ | −0.640 | −0.480 | −0.320 | −0.160 | 0.000 | 0.160 | 0.320 | 0.480 | 0.640 |
| $\Delta Rn$ | 0.000 | 0.074 | 0.126 | 0.153 | 0.160 | 0.147 | 0.115 | 0.066 | 0.000 |
| Dn | 0.640 | 0.486 | 0.343 | 0.221 | 0.160 | 0.217 | 0.340 | 0.485 | 0.640 |

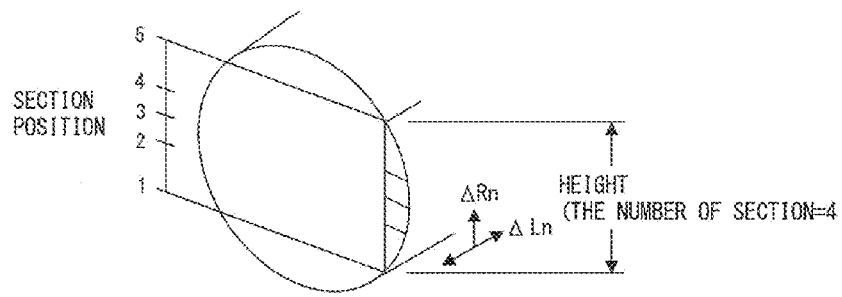
FIG.9A
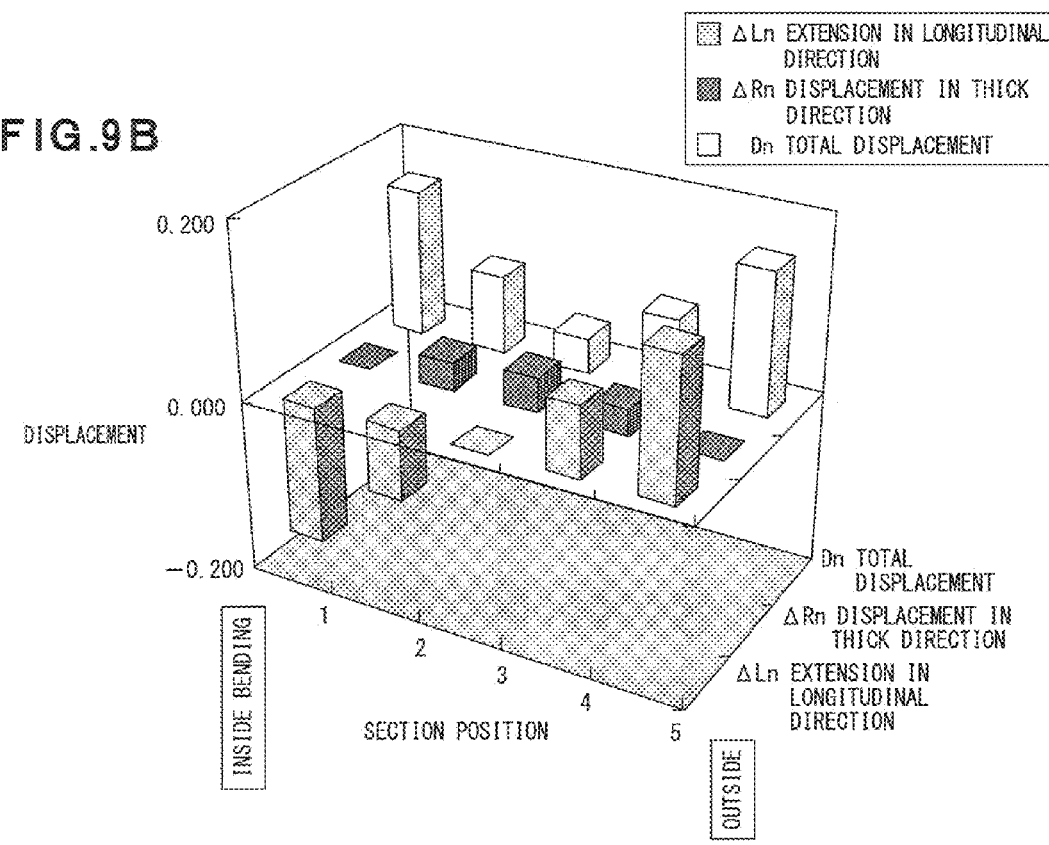
FIG.9B
FIG.9C
|  | 1 | 2 | 3 | 4 | 5 |
|---|---|---|---|---|---|
| $\Delta Ln$ | -0.160 | -0.080 | 0.000 | 0.080 | 0.160 |
| $\Delta Rn$ | 0.000 | 0.031 | 0.040 | 0.029 | 0.000 |
| Dn | 0.160 | 0.086 | 0.040 | 0.085 | 0.160 |

METHOD OF CULTIVATING CELL OR TISSUE

CROSS-REFERENCE TO RELATED APPLICATIONS

This application is a National Phase filing under 35 U.S.C. §371 of PCT/JP2007/062587 filed Jun. 22, 2007, which claims priority to Patent Application No. 2006-189732, filed in Japan on Jul. 10, 2006. The entire contents of each of the above-applications are incorporated herein by reference.

BACKGROUND OF THE INVENTION

1. Field of the Invention

The present invention relates to cultivation of a cell or tissue in the fields of regeneration medicine and tissue engineering, and relates to a method of three dimensional tissue cultivation for a three dimensional tissue and or organ regeneration. Concretely, the above cultivating method is executed with any of a cell, a cell scaffold and an ECM (extracellular matrix) that a cell generates, as a cell construct. There may be a case where the above cultivating method is executed with addition of a culture fluid, other additives, a growth factor, a chemical and so on.

In short, the cultivating method of the present invention differs from the conventional static cultivation. The cultivating method of the present invention is a method relating to three dimensional cultivation where physical action is used together. The cultivating method is for realizing objective regeneration tissue by differentiation induction or dedifferentiation deterrence along with that growth, cell migration and substance migration are promoted to improve survivability of a cell by stimulating a cell of a cell construct aggressively and displacing a cell construct.

2. Description of the Related Art

For cultivation of a cell or tissue, a method of imparting physical stimulation such as pressure and tension to a cell or tissue to be cultivated is studied, and various bioreactors and so on are suggested. Two dimension cultivation (plane cultivation) is a cultivating method using a flat bottomed culture carrier, and in general, is a static cultivating method in an incubator. Suspension cultivation is a method of cultivating a non-adherent cell being suspended. This method is also a static cultivating method in an incubator. Three dimension cultivation is a method that is generally executed such that a cell scaffold where a cell is disseminated is left still in an incubator to be cultivated. It is general for the three dimension cultivation (using a bioreactor) that a cell is made to adhere to or is enclosed by a cell scaffold to process stirring of a culture fluid and so on. It is conceived that in the three dimension cultivation of a cell scaffold, physical action such as pressure, compression, tension and shear are imparted to a cell. A cultivation apparatus for imparting physical action is called "a bioreactor", "a tissue engineering processor", etc. This apparatus is being into practical utilization as a cell/tissue cultivation apparatus in vitro for cultivation experiments of tissue engineering and regeneration medicine.

Concerning such bioreactor having functions of cultivating a cell or tissue, and imparting physical displacement, stress and stimulation used in the cultivating, a method for cultivating a cell or tissue and an apparatus therefor are disclosed in Japanese Laid-open Patent Publication No. 2001-238663 (Abstract, etc.) as an example of using pressure and oscillation (supersonic wave), a method for in vivo, ex vivo and in vitro repair and regeneration of cartilage and collagen, and bone remodeling is disclosed in Published Japanese Translations of PCT International Publication for Patent Application No. 2004-512031 (Abstract, etc.) as an example of using pressure, a cell and tissue-cultivating apparatus is disclosed in Japanese Laid-open Patent Publication No. 2002-315566 (Abstract, etc.) as an example of using shear force, a cell and tissue-cultivating device is disclosed in Japanese Laid-open Patent Publication No. 2003-061642 (Abstract, etc.) as an example of using tensile force, a cell and tissue cultivation apparatus is disclosed in Japanese Laid-open Patent Publication No. 2003-180331 (Abstract, etc.) as an example of using compression force, a device for cultivating cell is disclosed in Japanese Laid-open Patent Publication No. H09-313166 (Abstract, etc.) as an example of using shear force, a loading device of extending and contracting stimulation for cultivating a cell by using a silicone belt is disclosed in Japanese Laid-open Patent Publication No. H10-155475 (Abstract, etc.) as an example of using tensile force, and an apparatus executing sterilization, inoculation, cultivation, preservation, transport and test of tissue and a synthetic or natural vascular graft, and a method therefor are disclosed in Published Japanese Translations of PCT International Publication for Patent Application No. H11-504216 (Abstract, etc.) as an example of using both tension and shear. A cultivating method where distortion is given to cells held on membranes by the membranes is disclosed in Japanese Laid-open Patent Publication No. 2005-143343 (Abstract, etc.). A semi-permeable membrane being used for cultivation is disclosed in International Publication Pamphlet No. WO 2006/015304 A2 (Abstract, etc.) and Published Japanese Translations of PCT International Publication for Patent Application No. 2000-513214 (Abstract, etc.). Imparting of various kinds of physical action and stimulation, and using of a semi-permeable membrane are tried for cultivation of a cell, etc.

There are regions receiving many kinds of stress in the human body. Tissue used for repairing these regions is different according to the regions. For example, a disc, a meniscus, a bone, fiber cartilage and a valve of a heart receive bending stress in vivo. This bending stress is different from simple pressure, compression, tension, shear, etc. It is unnecessary that tissue cultivated by stimulus factor such as a simple pressure, compression, tension and shear are applied to a region receiving such bending stress.

The inventors of the present invention conceives that bending is so useful for growth, etc. of a cell or tissue as stimulation or a load imparted to a cell or tissue to be cultivated. The present invention is based on such concept. Concerning this bending, there is no disclosure in the above patent documents and is no suggestion thereabout.

SUMMARY OF THE INVENTION

An object of the present invention relates to a method for cultivating a culture including a cell and/or tissue, and is to provide a method for cultivating a cell and/or tissue proper for a region of a body of a human being and so on.

To achieve the above object, the present invention relates to a method for cultivating a culture including a cell and/or tissue. By virtue of applying bending force to a culture including a cell and/or tissue to thereby bent the culture, concretely by virtue of curving the culture, continuous compression and extension in a direction of thickness from a concave portion toward a convex portion thereof are induced. The physical stimulation and deformation not attained by conventional pressurization, shear and tension, then can be loaded on the culture to thereby realize the culture appropriate for restoration of tissue at a region accompanied by bending.

To achieve the above object, a first aspect of the present invention there is provided a cultivating method of a culture including a cell and/or tissue, comprising loading bending motion to the culture.

To achieve the above object, preferably, in the above cultivating method, the bending motion may include a process that brings the culture into a curving state.

To achieve the above object, preferably, the above cultivating method may comprise disposing the culture on a bed able to be curved, wherein the bending motion may be executed by the medium of the bed.

To achieve the above object, preferably, in the above cultivating method, the bed at its both ends may be movably held, and the bed may be curved by imparting a load to a center part of the bed.

To achieve the above object, preferably, in the above cultivating method, the culture may be sealed by a semi-permeable membrane.

To achieve the above object, preferably, in the above cultivating method, the bending motion may be executed periodically or intermittently.

To achieve the above object, preferably, in the above cultivating method, the culture may include any of a cell, a cell scaffold, an extracellular matrix produced by the cell, and a culture fluid.

To achieve the above object, preferably, in the above cultivating method, the culture may be a three-dimensional culture scaffold where a cell is disseminated.

To achieve the above object, preferably, in the above cultivating method, the culture may include a gel substance.

To achieve the above object, preferably, in the above cultivating method, the three-dimensional culture scaffold may be a bioabsorbable material.

To achieve the above object, preferably, in the above cultivating method, the gel substance may be a bioabsorbable material.

To achieve the above object, preferably the above cultivating method may comprise any of imparting continuous tension to the culture; imparting intermittent tension to the culture; or imparting continuous or intermittent tension to the culture periodically.

To achieve the above object, preferably, the above cultivating method may comprise a process that pressures the culture, wherein pressure to the culture may be given continuously or intermittently, or may be changed periodically or irregularly.

Features and advantages of the present invention are as follows.

(1) Since displacement (stress) such as bending a culture is applied in cultivation, cultivation of a culture can be promoted. For example, culture can be used for regeneration of tissue receiving bending force in vivo like discs, etc.

(2) It can be expected to prevent a stem cell from differentiating and prevent a tissue cell from dedifferentiating.

(3) If tissue structure and so on have directionality, the direction thereof can be uniform, and a culture equal to tissue in vivo can be obtained.

(4) A necessary tissue can be cultivated by bending action without other kinds of physical action such as pressure, or with the minimum thereof.

(5) Cell migration can become easy.

(6) Nutrients and oxygen can be osmosed in the interior to a three dimensional cell construct.

(7) Discharging waste products becomes easy.

(8) If a semi-permeable membrane separates a part where a cell exists from a part of a culture fluid, shear force by flow of the culture fluid is excluded, and culture can be made with an action that is limited to bending and pressure.

(9) If a semi-permeable membrane separates a part where a cell exists from a part of a culture fluid, cells become a spheroid without a scaffold, and three dimensional tissue can be realized.

Other objects, features and advantages of the present invention are more clearly understood by referring to the attached drawings and each of the embodiments.

BRIEF DESCRIPTION OF THE DRAWINGS

FIG. 7A is an analysis diagram relating to displacement inside a gel column at a position in height;

FIG. 7B is an analysis diagram relating to displacement inside a gel column at a position in height;

FIG. 7C is an analysis diagram relating to displacement inside a gel column at a position in height;

FIG. 8A is an analysis diagram relating to displacement inside a gel column at a position in height;

FIG. 8B is an analysis diagram relating to displacement inside a gel column at a position in height;

FIG. 8C is an analysis diagram relating to displacement inside a gel column at a position in height;

FIG. 9A is an analysis diagram relating to displacement inside a gel column at a position in height;

FIG. 9B is an analysis diagram relating to displacement inside a gel column at a position in height;

FIG. 9C is an analysis diagram relating to displacement inside a gel column at a position in height;

DETAILED DESCRIPTION OF THE PREFERRED EMBODIMENTS

First Embodiment

A method for cultivating a cell or tissue according a first embodiment of the present invention will be described.

A cell construct 2 (FIG. 3) is used as an example of a culture in the method for cultivating cell or tissue. The cell construct 2 includes the any of a cell, a cell scaffold and an extracellular matrix that the cell generates. There may be a case where a culture fluid, other additives, a growth factor, a chemical and so on may be added. For example, the cell construct 2 may be structured by a culture fluid where cells are suspended, a complex of a three dimensional scaffold where cells are disseminated, and a gel substance or other scaffolds, and the culture fluid and the complex being enclosed in a bag or a tube made from a semi-permeable membrane. A three dimensional scaffold and a gel substance are composed of, for example, a bioabsorbable material.

The above semi-permeable membrane enclosing the cell construct 2 is made in accordance with a size of a molecule that can pass through the semi-permeable membrane. For instance, a semi-permeable membrane is selected out of semi-permeable membranes whose transmission molecular weight is from 100 (Da(Dalton)) to 1000 (kDa) to be used. That is, if a semi-permeable membrane such that substance of a low molecule like nutrition in a culture fluid, a necessary gas such as oxygen and waste matters exhausted by a cell exhausts pass to enclose cells and a polymeric extracellular matrix are not allowed to pass is selected, and a cell, nutrition and oxygen can be supplied while preventing an outflow of a cell and an extracellular matrix, and effective cultivation is realized.

Figure 1:
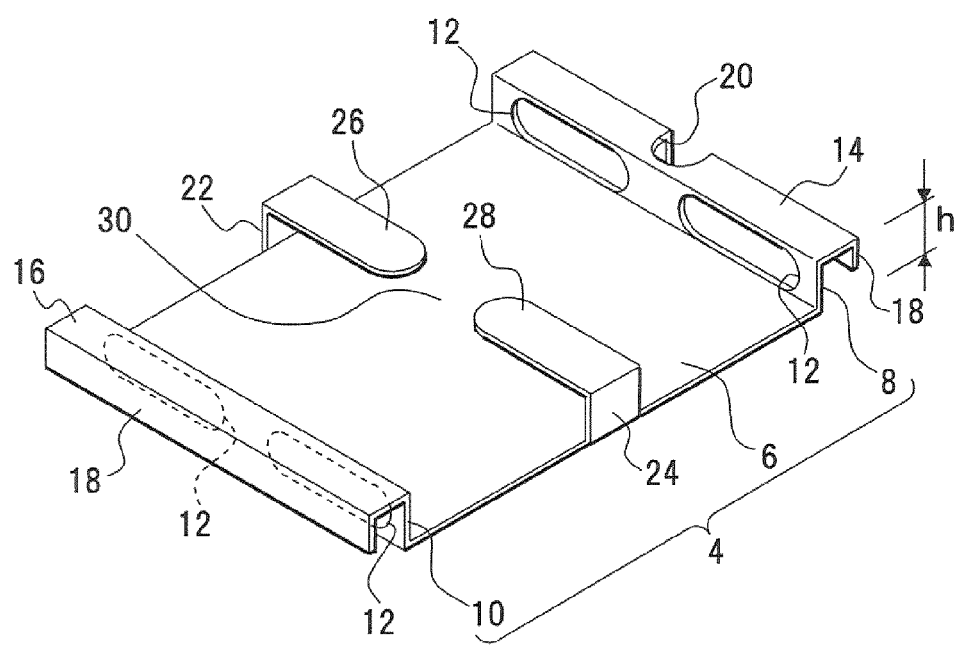
FIG. 1 depicts a structural example of a culture bed according to a first embodiment.

A culture bed 4 is used for culture of the cell construct 2. FIG. 1 depicts a structural example of this culture bed.

This culture bed 4 holds the cell construct 2, and a means for imparting motion to the cell construct 2. The culture bed 4 constitutes a function unit transmitting a displacement movement to the held cell construct 2, and by elasticity that the culture bed 4 has, returning a state of the cell construct 2 to a state before the displacement movement.

A disposing part 6 where two cell constructs 2 can be disposed in parallel is included in the culture bed 4. The disposing part 6 is a plate-shaped part having an area and a shape where each cell construct 2 is disposed in parallel, and made from an elastic member for imparting bending motion to each cell construct 2. As an elastic member, for example a stainless steel sheet for a spring or other materials that have high spring are used. In this case, the whole culture bed 4 may be formed by an elastic member, or the disposing part 6 that enables bending motion or a part thereof may be formed by an elastic member. The deposing member 6 is not limited to a flat plate-shaped part, and may be net. The disposing part 6 may structure of deposing single cell construct 2, or of allowing three or more cell constructs 2 to be disposed.

The disposing part 6 is a rectangular shape. At end parts in a longer direction thereof, rectangular standing walls 8 and 10 are formed. Each of the standing walls 8 and 10 is perpendicular to the disposing part 6, and in the standing walls 8 and 10, elliptic through holes 12 corresponding to each cell construct 2 are formed. These through holes 12 fix both ends of the cell construct 2. Each of the standing walls 8 and 10 is set in a predetermined height h according to a size of each cell construct 2.

At a top of each of the standing walls 8 and 10, supporting faces 14 and 16 that face the disposing part 6 in parallel and have a constant width are formed. From each supporting face 14 and 16, turnover 18 is formed in parallel to each of the standing walls 8 and 10 by turning a part of each supporting face 14 and 16. Each turnover 18 reinforces each supporting face 14 and 16, and each standing wall 8 and 10. That is, sufficient strength can be obtained if each supporting face 14 and 16, and each standing wall 8 and 10 are formed by the same board as the disposing part 6 which is made of a thin plate, and weight of the culture bed 4 can be saved. In the culture bed 4 of the embodiment, a U-formed notch 20 corresponding to a fixing pin not shown is formed in order to fix the supporting face 14.

From middle edges of the disposing part 6, supporting walls 22 and 24 that support sides of the disposed cell construct 2 are formed. From a top of each supporting wall 22 and 24, holding parts 26 and 28 that cover a top surface of the cell construct 2 are formed. Each supporting wall 22 and 24 is a wall perpendicular to the disposing part 6. The height thereof is the same as the above described standing walls 8 and 10. Each holding part 26 and 28 constructs a parallel face with the disposing part 6. The cell construct 2 is disposed in a gap between the disposing part 6, and each holding part 26 and 28. An end part of each holding part 26 and 28 constructs a curve face. Between the curve faces, a gap 30 for attaching and detaching the cell construct 2 is set.

Figure 2:
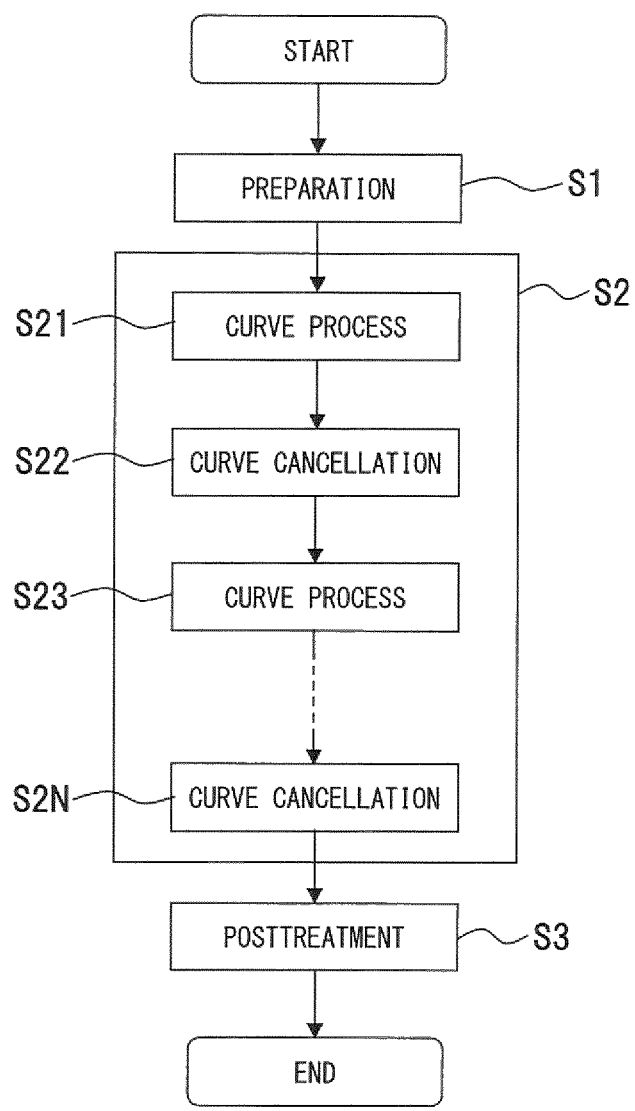
FIG. 2 is a flowchart showing processing procedure of cultivation.
Figure 3:
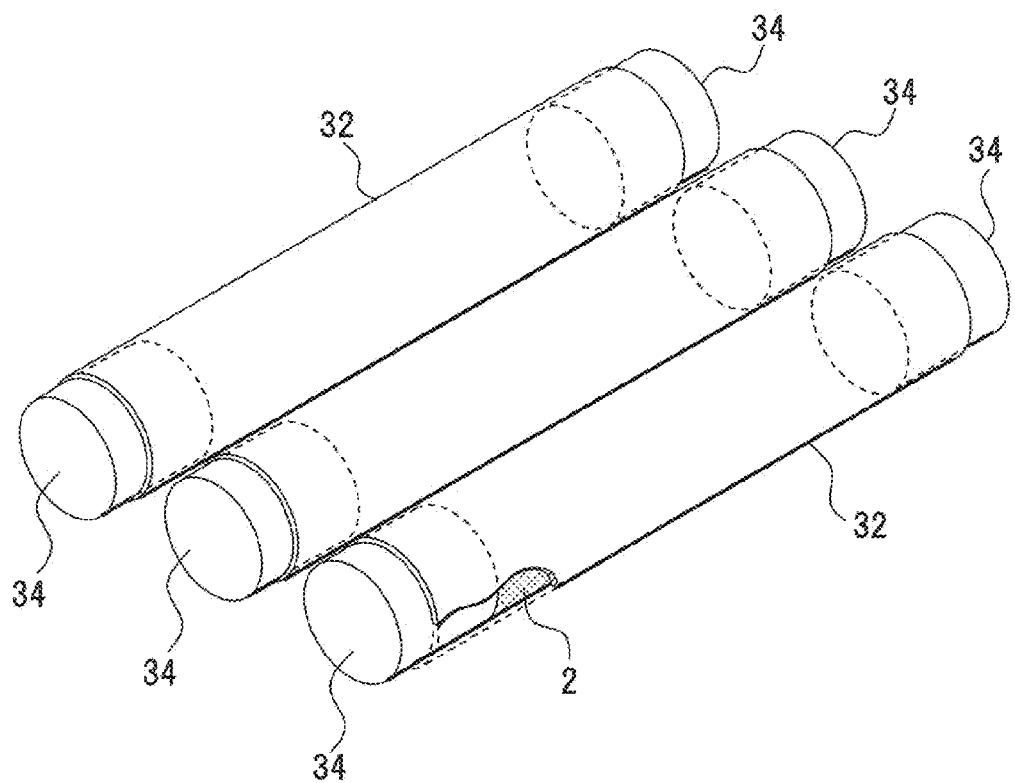
FIG. 3 depicts a form of a cell construct to be cultivated.
Figure 4A:
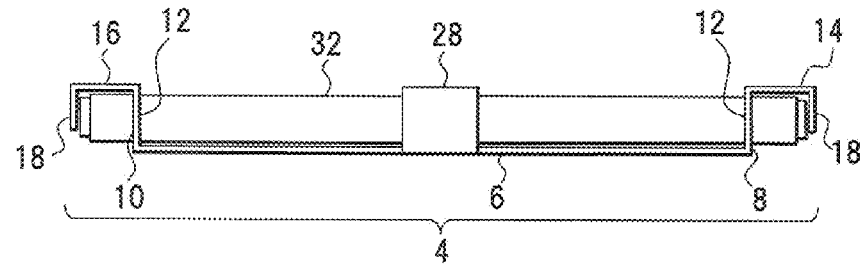
FIG. 4A depicts a state that a cell construct is disposed on a culture bed.
Figure 4B:
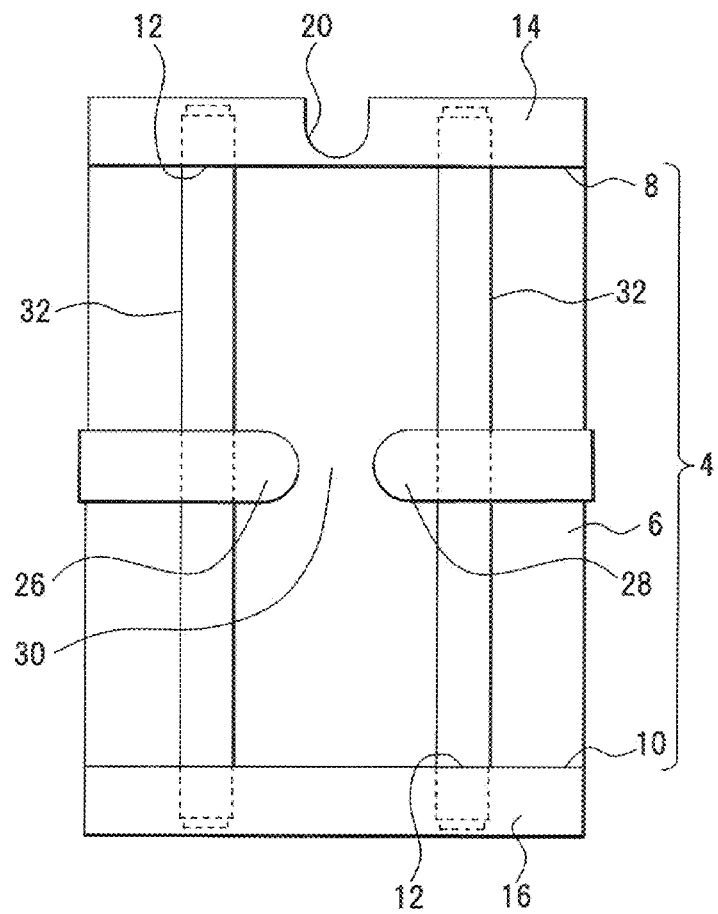
FIG. 4B depicts a state that a cell construct is disposed on a culture bed.
Figure 5A:
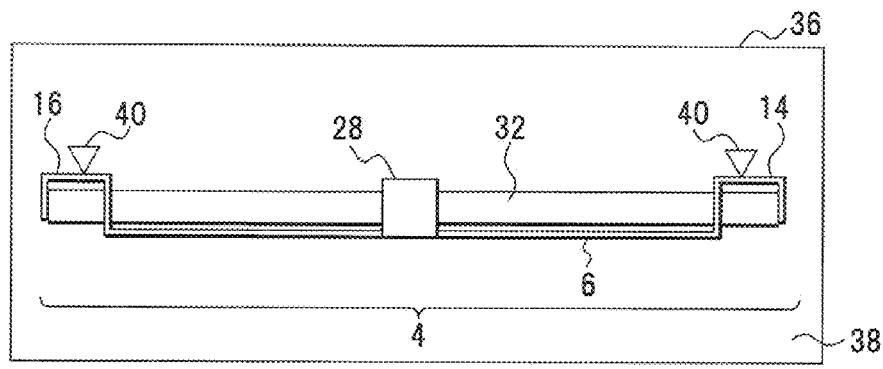
FIG. 5A depicts imparting bending motion to a cell construct and cancellation thereof.
Figure 5B:
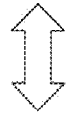
FIG. 5B depicts imparting bending motion to a cell construct and cancellation thereof.
Figure 5B:
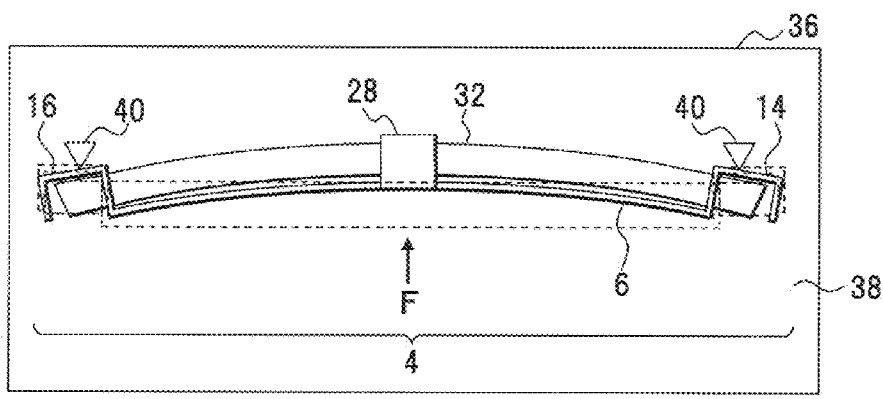

A cultivating method of the cell construct 2 will be described with referring to FIGS. 2, 3, 4A, 4B, 5A and 5B. FIG. 2 is a flowchart showing processing procedure of cultivation, FIG. 3 depicts a form of a cell construct to be cultivated, FIGS. 4A and 4B depict disposing a cell construct on a culture bed and FIGS. 5A and 5B depict imparting bending motion to a cell construct and cancellation thereof.

As shown in FIG. 2, a cultivation process of the cell construct 2 includes a preparation (step S1), a cultivation process (step S2) and a posttreatment (step S3). The preparation includes forming the cell construct 2, an enclosing process to a semi-permeable membrane, etc. The cultivation process includes a bending motion process. In the cultivation process, a curve process (step S21), curve cancellation (step S22), a curve process (step S23) . . . curve cancellation (step S2N) are repeatedly executed. The posttreatment includes taking out of the cell construct 2 whose cultivation is ended from the culture bed 4 and so on.

(1) Preparation (step S1)

In forming of the cell construct 2, tissue or a cell is taken out from in vivo, and the taken tissue is resolved by enzymes and so on to select a necessary cell. If the selected cell must be grown, a process of increasing the number of the cell may be executed in the preparation by monolayer culture and so on. The cell construct 2 is made from the obtained cell, and the combination of a culture fluid, a hydro-gel or a gel scaffold. As an infinite construct, a cell may be suspended in a culture fluid or a hydro-gel, or a cell may be mixed with a gel scaffold. As a finite construct, a cell may be suspended in a culture fluid, and the culture fluid is entered into a cell scaffold such as a collagen sponge and a chitosan sponge to be attached to the cell, or, a cell in a sol state is mixed into a scaffold, and the scaffold is entered in a cell scaffold such as collagen sponge and chitosan sponge to attach the cell and to gel the cell. A growth factor or chemist may be added if necessary.

As shown in FIG. 3, the cell construct 2 of a culture is enclosed into a tube 32 that is made from a semi-permeable membrane to be cultivated. A stopper 34 made from, for example, a semi-permeable membrane is provided at one end of the tube 32 of a semi-permeable membrane. The above cell construct 2 is put into the tube 32 from another end thereof, and by shutting the another end by the stopper 34 as well, the cell construct 2 is sealed. The size of the tube 32 enclosing the cell construct 2 may change dependently on an object of a culture and a kind of the cell construct 2, etc.

As shown in FIGS. 4A and 4B, the cell construct 2 sealed in the tube 32 is disposed on the disposing part 6 of the culture bed 4. Concerning a disposing process to the culture bed 4, the tube 32 enclosing the cell construct 2 is passed the gap 30 provided between the holding parts 26 and 28, and both ends of the tube 32 is passed through the through holes 12 provided in each standing wall 8 and 10. And the tube 32 is disposed such that a middle part thereof positions between the disposing part 6 and the holding part 26 or 28. In the embodiment, two tubes 32 are disposed. The number thereof is not limited to the embodiment. Also, in the embodiment, both ends of the tube 32 are inserted into the through holes 12 to be fixed. The tube 32 may be held to the culture bed 4 by, for example, a clip for the tube, etc. in accordance with the size of a tube.

By disposing the tube like the above, each through part 12 and holding part 26 and 28 hold the tube 32, for example, against curve of the culture bed 4 by force applied to the bottom side of the culture bed 4 and cancellation thereof, and the tube 32 is made to curve and is made restoration movement with the culture bed 4 to enable bending motion in a culture process described below.

(2) Culture process (step S2)

In the culture process, as shown in FIG. 5A, the cell construct 2 enclosed in the tube 32 is transferred to a culture chamber 36 that is a culture space with the culture bed 4. A culture fluid 38 is supplied into the culture chamber 36. After the cell construct 2 is set into the culture chamber 36, the culture chamber 36 is made into a sealing state by, for example, a cover for preventing the culture fluid 38, etc. from flowing out, and preventing contamination from an outside. The supporting faces 14 and 16 of the culture bed 4 disposed in the culture chamber 36 is held by the supporting member 40. For the above, vertical difference does not occur to the culture bed 4 by applying following described force F from a back side, thus the culture bed 4 and the tube 32 can be curved. The culture chamber 36 may have a structure of maintaining its sealing state, and such that the culture fluid 38 is circulated to be supplied during the culture process. In this case, the culture fluid 38 may be continuously circulated in the culture chamber 36, or may be periodically exchanged.

If the force F is loaded from the back side of the culture bed 4 by, for example, a lever not shown, as shown in FIG. 5B, the disposing part 6 of the culture bed 4 is curved upwardly by the force F. By this curve, the tube 32 on the disposing part 6 is also curved. That is, bending occurs to the cell construct 2. If the force F is released from this bending state, the disposing part 6 of the culture bed 4 is restored to an original form by its elasticity to be flat. Thus, the cell construct 2 on the disposing part 6 switches into a flat state to be in a state shown in FIG. 5A again. In this case, on an upper face of the tube 32, the holding parts 26 and 28 of the culture bed 4 exist. The tube 32 that is deformed to be upwardly convex is pressed onto the through holes 12 where both ends of the tube 32 are passed and the holding parts 26 and 28 in accordance with the restoration of the disposing part 6 to flatten dependently on the restoration of the disposing part 6. As described above, the same amount of displacement as an amount of displacement of curve and flattening of the culture bed 4 is given to the cell construct 2 enclosed in the tube 32 by the through holes 12 and the holding parts 26 and 28. Thus, by controlling an amount of movement by the adding force F, an amount of bending motion given to the cell construct 2 can be controlled, too.

Such bending motion is repeated (step S21-step S2N), a cell is propagated in the tube 32 as necessary culture time passes, and an extracellular matrix and so on are generated to regenerate infinite or finite neogenetic tissue. A period and magnitude of bending motion, a movement schedule, temperature setting in the culture chamber 36, etc. are set by an optimum pattern and so on in advance of a start of the culture process. The settings may be optionally done in accordance with a cultivating state of a cell or tissue. If necessary, the structure may be made that pressure is applied into the culture chamber 36 to be cultivated.

Like the above, in case where the tube 32 of a semi-permeable membrane is used for cultivation, while shear stress generated between a culture fluid and a culture is prevented and flowing out of a cell and an extracellular matrix is prevented, nutrition and oxygen can be supplied and efficient culture is realized. However, because a semi-permeable membrane becomes resistance to passing nutrition, there is a risk that an obstacle to supplying nutrition occurs. As described above, by adding bending motion, inside displacement rises actively, difference of pressure occurs, nutrition is easily moved, and physical stimulation is imparted to a cell. For this, the cell construct 2 that a blood vessel is still not generated and tissue without a blood vessel can be cultivated with bending motion that acts for a blood vessel and a heart.

(3) Posttreatment (step S3)

The cell construct 2 whose culture is completed is taken out from the culture chamber 36 with the culture bed 4 (FIG. 5A). The tube 32 enclosing the cell construct 2 is taken out from the culture bed 4, and neogenetic tissue such as cells propagating therein and a generated extracellular matrix are taken out. A quality inspection and so on are executed on the taken neogenetic tissue, and the neogenetic tissue is preserved till utilization for treatment of a human body and so on.

The cultivated neogenetic tissue is directly transplanted to a human body by means such as suture if finite tissue. If infinite tissue, the neogenetic tissue is processed such as injection into a deficit part, and application or forming to be fixed in response to a form of tissue. Then amalgamation with tissue therearound in vivo allows being organized.

Figure 6A:
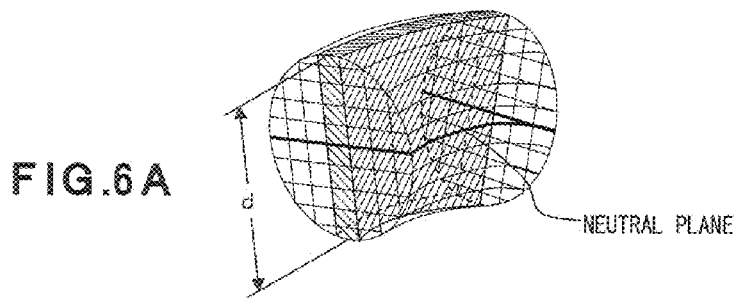
FIG. 6A is a view relating to an analysis of force and displacement that a cell construct receives in a bending state.
Figure 6B:
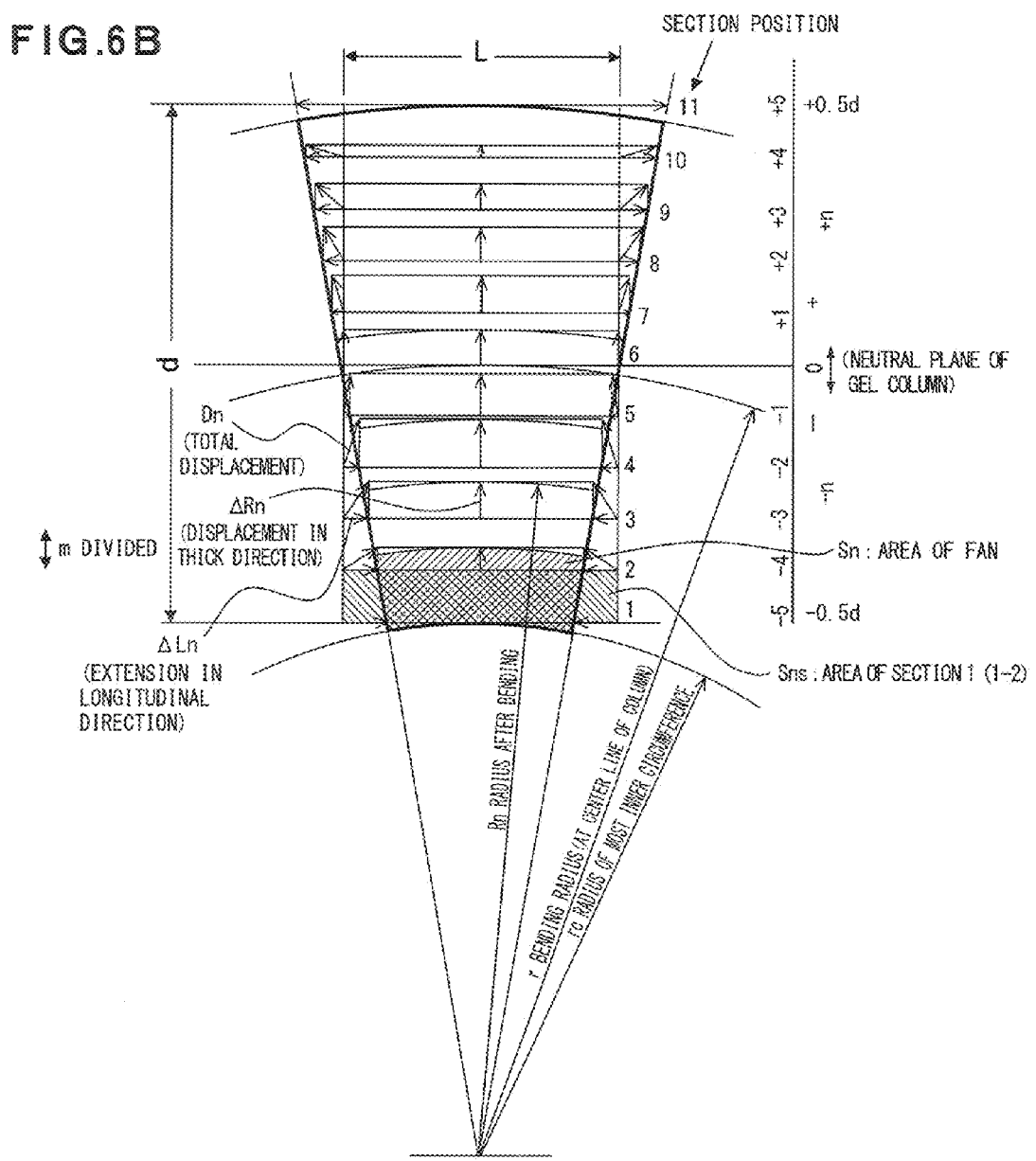
FIG. 6B is a view relating to an analysis of force and displacement that a cell construct receives in a bending state.

Bending motion and cultivation in the cultivation process of the cell construct 2 will be described in FIGS. 6A and 6B. FIGS. 6A and 6B are a view used for an analysis of force and displacement that a column cell construct receives in a bending state.

The culture bed 4 is held at a predetermined position not to differ vertically, etc. in the culture chamber 36 as described above. The cell construct 2 is also fixed to the culture bed 4. Thus, as shown in FIG. 5B, if the force F is applied from the back side of the culture bed 4, the disposing part 6 of the culture bed 4 is curved upwardly, and the cell construct 2 deforms along the culture bed 4.

If an object is to be bent, bending stress occurs. By bending an object, bending strain occurs. Many kinds of strain occur inside a bent object. That is, as shown in FIG. 6B, tensile force acts on an outer circumference side of bending (an upper side of FIG. 6B), and the outer circumference side extends. Compression force acts on an inner circumference side thereof (a lower side of FIG. 6B) vice versa, and the inner circumference side shrinks. Considering a micro part in an object, at a position where micro parts adjoin with each other, difference occurs to displacement of extension and shrink. Shearing stress occurs thereto. Thereby, shearing strain occurs. As shown by a heavy line in FIG. 6A, there is so-called a neutral plane where a part of an object has no displacement of extension and shrink (0). With including the neutral place, shearing strain occurs to all of positions. The shearing strain occurs in a regular direction.

A sectional area is changed by bending to change inside pressure. By changing a shape of a section, parts occur where pressure rises and falls inside an object. Since an outer circumference is tensed and an inner circumference is compressed, a part of the inner circumference is high pressure, and a part around the outer circumference is low pressure.

That is, tension, compression, shear and pressure act variously on bending. If bending motion is acted on the cell construct 2, an inside of the cell construct 2 is slightly deformed by tension, compression, shear and pressure. Here, since a contraction percentage of a liquid by pressure is so particle that the contraction percentage can be ignored, strain by bending motion can cause huge strain much greater than strain caused by a method of repeatedly applying pressure to the cell construct 2. From this, action of bending can bring effects such as movement and supply of a cell, nutrition, oxygen and waste matters more, and since shear force of tension and compression in a specific direction is generated for a bending direction, a formed tissue can be aligned uniformly.

Therefore, a cell appropriate for bending motion can be promoted to be propagated, and tissue whose alignment resembles to tissue in vivo can be cultivated. Along with bending, applying pressure can enlarge the effects.

As a model of the cell construct 2, extension generated when a gel column bends, etc. will be analyzed with referring to FIGS. 6A and 6B.

As shown by oblique lines in FIG. 6A, FIG. 6B showing a section in a longitudinal direction of a gel column whose diameter before bending is d is considered. A lateral length before deformation is shown by L. A center line of the gel column is bent such that a curvature radius thereof becomes r. The height of the gel column before bending is d (diameter). The d is partitioned into m sections from inside to an outside of bending. The center line of the gel column is shown by 0, and sections are numbered as −n toward an inside of the gel column, and as +n toward an outside thereof. In FIG. 6B, as one example, the gel column is divided into ten sections, and section positions from an inside one to an outside eleven of bending are shown by a contact point of each line dividing the gel column and a side face of the gel column being a calculation position of displacement.

Extension in a longitudinal direction is shown by ΔLn, displacement in a thick direction is shown by ΔRn and total displacement is shown by Dn. Displacement in a longitudinal direction (circumferential direction) by bending is analyzed. The gel column of length L shrinks at the inner circumference, and extends at the outer circumference. If the center line of the column before bending is a neutral plane, compression stress and tensile stress are equal. A curvature radius $r_n$ of the nth section is (Formulae 1)

$$r_n = r + \frac{n}{m}d \quad (1)$$

A chord length of the nth section is (Formulae 2)

$$\hat{L}n = L \times \frac{r_n}{r} \quad (2)$$

Extension in a longitudinal direction ΔLn is (Formulae 3)

-continued $$\Delta Ln = \hat{L}n - L = L \times \frac{r_n}{r} - L = L\left(\frac{r_n}{r} - 1\right) \quad (3)$$

If formula (1) is substituted to formula (3), (Formulae 4)

$$\Delta Ln = L\left(\frac{r + \frac{n}{m}d}{r} - 1\right) = L \cdot \frac{n \cdot d}{m \cdot r} \quad (4)$$

Displacement ΔRn in a thick direction (a direction of a curvature radius) is analyzed. If n sections from the most inside part when bending are bent, the sections that were a rectangle before displacement become a fan with retaining its area. When the gel column is bent, as described above, since a longitudinal direction changes, in response thereto, thickness thereof changes. With using this method, displacement in a thick direction is calculated. Distance $r_o$ from the center to the most inside face when bending is (Formulae 5)

$$r_o = r - \frac{1}{2}d \quad (5)$$

An area of a rectangle from the most inside section to the nth section Sns is (Formulae 6)

$$S_{ns} = \frac{n + \frac{m}{2}}{m} d \cdot L \quad (6)$$

Area of a fan from the most inside section to the nth section Sn is (Formulae 7)

$$S_n = \frac{L}{2\pi r}(\pi R_n^2 - \pi r_0^2) \quad (7)$$

If Sns and Sn maintain the same areas (Sns=Sn), by formula (6) and formula (7), (Formulae 8)

$$\left(\frac{n + \frac{m}{2}}{m}\right) \cdot d \cdot L = \frac{L}{2\pi r}(\pi Rn^2 - \pi r_0^2) \quad (8)$$

$$\pi Rn^2 - \pi r_0^2 = \frac{2\pi r \cdot d \cdot L\left(n + \frac{m}{2}\right)}{Lm}$$

$$\pi Rn^2 = \frac{2\pi r \cdot d \cdot L\left(n + \frac{m}{2}\right)}{Lm} + \pi r_0^2$$

$$R_n^2 = \frac{2r \cdot d\left(n + \frac{m}{2}\right)}{m} + r_0^2$$

If formula (5) is substituted to formula (8), (Formulae 9)
$$R_n^2 = \frac{2r \cdot d\left(n + \frac{m}{2}\right)}{m} + r^2 - rd + \frac{d^2}{4} = \frac{2rd \cdot n}{m} + r^2 + \frac{d^2}{4} \quad (9)$$
$$R_n = \sqrt{\frac{2rd \cdot n}{m} + r^2 + \frac{d^2}{4}}$$

As to the nth section before bending, distance $r_n$ from the center of a curvature is (Formulae 10)
$$r_n = r + \frac{n}{m}d \quad (10)$$

From this, displacement when bending $\Delta Rn$ is (Formulae 11)
$$\Delta Rn = R_n - r_n \quad (11)$$
$$\Delta Rn = \sqrt{\frac{2r \cdot d \cdot n}{m} + r^2 + \frac{d^2}{4}} - \left(r + \frac{n}{m}d\right)$$

Therefore, total displacement Dn is calculated from (Formulae 12)
$$D_n = \sqrt{\Delta Ln^2 + \Delta Rn^2} \quad (12)$$

With using the above analysis, displacement inside the gel column is shown in FIGS. 7A, 7B, 7C, 8A, 8B, 8C, 9A, 9B and 9C. FIGS. 7A, 7B and 7C are analysis diagrams relating to displacement inside a gel column at a center position in height ten (=diameter d, the number of section=10), FIGS. 8A, 8B and 8C are analysis diagrams relating to displacement inside a gel column at a position in height eight (the number of section=8)(a position differing from the center) and FIGS. 9A, 9B and 9C are analysis diagrams relating to displacement inside a gel column at a position in height four (the number of section=4) (a position further differing from the center).

In detail, a change when the gel column of ten in diameter (d=10) is bent at a curvature radius 50 (r=50) is analyzed. The column is divided into ten sections vertically and horizontally respectively. Displacement of length thereof is shown by a value for ten (L=10). Graphs show the cases where the height is ten (a section dividing the center of a circle, FIG. 7A), the height is eight (FIG. 8A), and the height is four (FIG. 9A) when the gel column is seen from a circular face side of the column. A section position representative of a calculated position of displacement is shown in a horizontal axis, total displacement (Dn), displacement in a thick direction ($\Delta Rn$) and extension in a longitudinal direction ($\Delta Ln$) are shown in a vertical axis, and an amount of displacement is shown in height.

From the above analyzed result, it is determined that if the column is bent, difference in size and a direction of displacement is inevitable between a point on a circle section of the column and an adjacent point thereto. By the difference, shear stress occurs to every part of the column. Note that to points on a line in a longitudinal direction, the equivalent displacement and stress occur.

Second Embodiment

Figure 10:
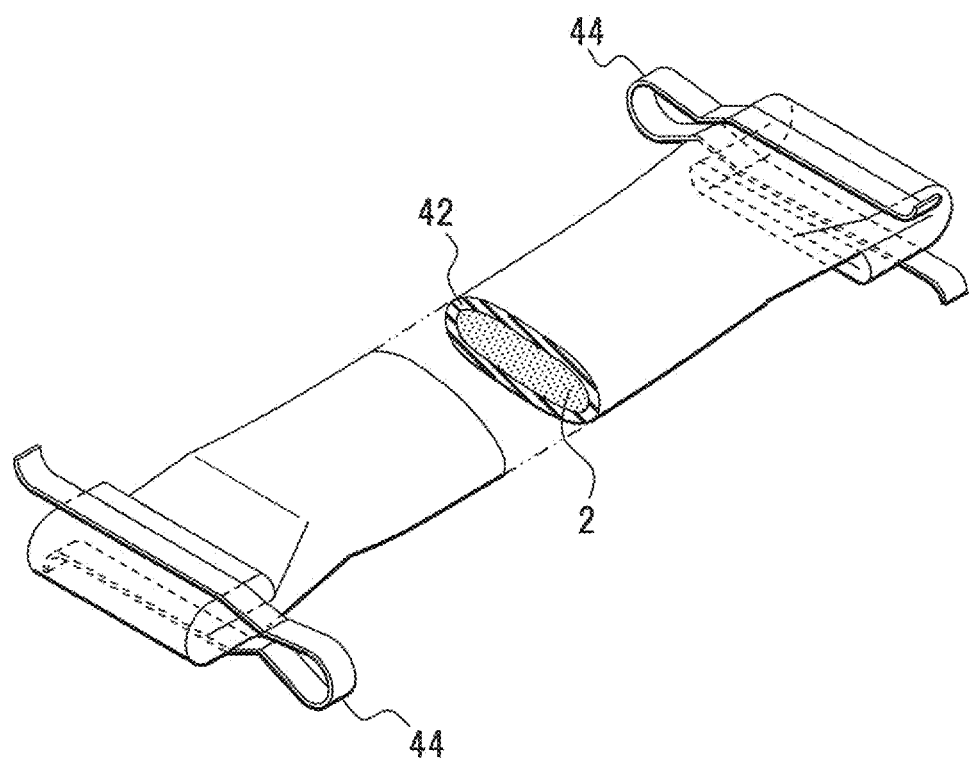
FIG. 10 depicts a form of a cell construct according to a second embodiment.
Figure 11:
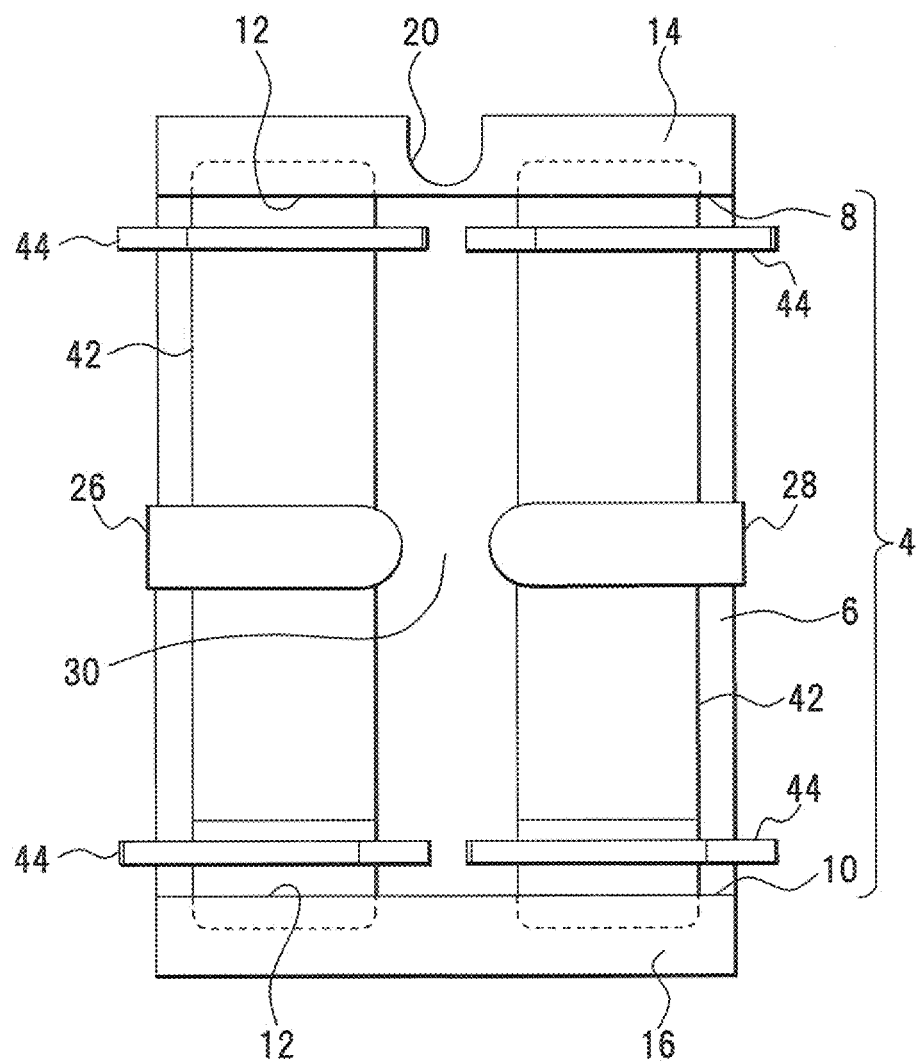
FIG. 11 depicts a state that a cell construct is disposed on a culture bed.

A method of cultivating a cell or tissue according to a second embodiment of the present invention will be described with referring to FIGS. 10 and 11. FIG. 10 depicts a form of a cell construct 2 according to a second embodiment, and FIG. 11 depicts a state that the cell construct 2 is disposed on a culture bed 4. In FIGS. 10 and 11, the same parts and the same components as those of the first embodiment are denoted by the same reference numerals.

In this embodiment, in the cultivating method according to the first embodiment, the infinite cell construct 2 is enclosed into a tube 42 of a semi-permeable membrane to be cultivated. For example, concerning the infinite cell construct 2 that a cell is suspended in a culture fluid or a hydro-gel, or that a cell is mixed with a gel scaffold, by tube 42 of a semi-permeable membrane not being a frame, infinite tissue is kept after cultivation, thus, tissue according to use such as insertion between tissue in vivo can be cultivated. The above gel substance is, for example, constructed of a bioabsorbable material.

Such cell construct 2 (FIG. 10) can be also cultivated by using the above described cultivating method (FIG. 2). In this case, in preparation, because of using the high flexible tube 42, a shape of an opening section is infinite. For sealing of both openings of the tube 42, flexibility that the tube 42 has is utilized, and in stead of the stopper 34 (FIG. 3), both openings thereof are sealed by clips 44 dedicated for the tube 42. That is, for preventing the cell construct 2 from flowing out of the tube 42, both ends of the tube 42 are turned down, and a process is executed such that overlapped parts are sealed by the clips 44. In order to prevent burst of the tube 42 by bending motion and make a space for moving the cell construct 2 in the tube 42, etc. a proper amount of the cell construct 2 is needed to be enclosed into the tube 42 not to be in a full state. The amount thereof depends on an objected amount of cultivation. For example, the cell construct 2 is enclosed so that a section of the tube 42 of a semi-permeable membrane becomes a shape of an ellipse.

The cell construct 2 enclosed in the tube 42 as described above is attached to the culture bed 4 as shown in FIG. 11. Concerning a disposing process to the culture bed 4 as well as the first embodiment, the tube 42 enclosing the cell construct 2 is passed the gap 30 provided between the holding parts 26 and 28, and both ends of the tube 42 are passed through the through holes 12 provided in each standing wall 8 and 10. And the tube 42 is disposed such that a middle part thereof positions between the disposing part 6 and the holding part 26 or 28. By disposing like this, bending motion to the cell construct 2 can be imparted in accordance with curve of the disposing part 6 of the culture bed 4 and cancellation thereof by bending motion in the above cultivation process.

In such structure, a cultivation process as well as that in the first embodiment allows cultivation of the infinite cell construct 2 as described above.

Concerning fixing the cell construct 2 and the culture bed 4, the structures may be done that for example, the clip 44 sandwiches the tube 42 and the culture bed 4 together, and that a clip for fixing the culture bed 4 is provided with the clip 44 together, other than the above structure.

Third Embodiment

Figure 12:
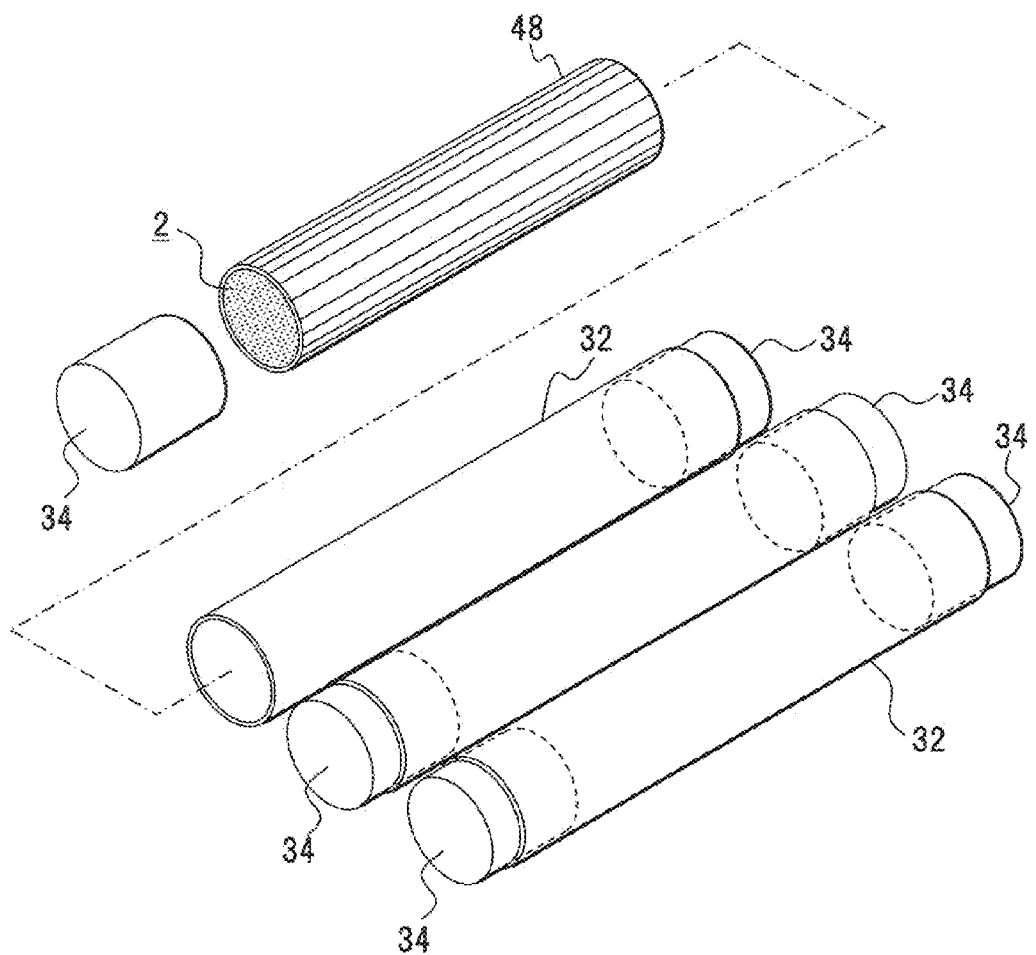
FIG. 12 depicts a form of a cell construct according to a third embodiment.

A method of cultivating a cell or tissue according to a third embodiment of the present invention will be described with referring to FIG. 12. FIG. 12 depicts a form of a cell construct according to a third embodiment. In FIG. 12, the same parts and the same components as those of the first embodiment are denoted by the same reference numerals.

In the embodiment, concerning the cultivating method according to the first embodiment, a cell is disseminated on a finite cell scaffold (three-dimensional scaffold) 48 and the finite cell construct 2 is made, then the finite cell construct 2 is enclosed into the tube 32 of a semi-permeable membrane to be cultivated. Concretely, a cell may be suspended in a culture fluid or a hydro-gel, or a cell may be mixed with a gel scaffold. As a finite construct, a cell may be suspended in a culture fluid, and the culture fluid is entered into a cell scaffold such as a collagen sponge and a chitosan sponge to be attached to the cell, or, a cell in a sol state is mixed into a scaffold, and the scaffold is entered in a cell scaffold such as collagen sponge and chitosan sponge to attach the cell and to gel the cell. A three dimensional scaffold and a gel substance are constructed of, for example, a bioabsorbable material. A cultivating method is the same as that in the above first embodiment, and the description thereof is omitted.

By the above structure, using the finite cell construct 2 in advance allows cultivation of neogenetic tissue that has a desired shape or size.

Fourth Embodiment

Figure 13:
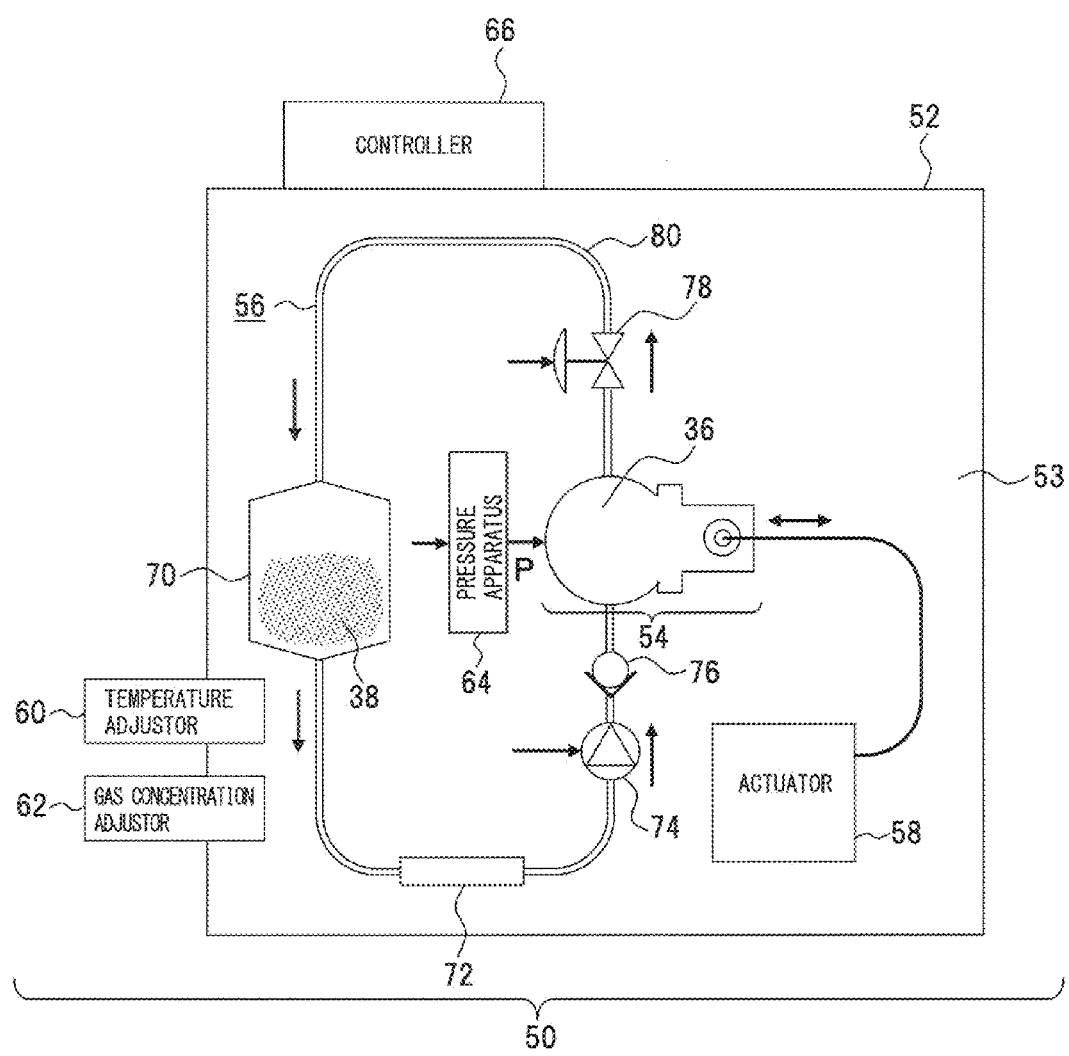
FIG. 13 depicts a system for cultivating a cell or tissue according to a fourth embodiment.

A cultivation system for a cell or tissue according to a fourth embodiment of the present invention will be described with referring to FIG. 13. FIG. 13 depicts a system for cultivating a cell or tissue. In FIG. 13, the same parts and the same components as those in the first embodiment are denoted by the same reference numerals, and descriptions thereof are omitted.

In the embodiment, in the method for cultivating a cell or tissue according to the first to the third embodiments, a culture system 50 is structured that a culture fluid is circulated, a fresh culture fluid is supplied at any time and temperature and pressure in a culture room, and concentration of a supplied mixed gas G, etc. are controlled to cultivate a cell or tissue.

In the culture system 50, an incubator 52 that is a culture apparatus is used. In a culture room 53 of the incubator 52, a culture unit 54, a culture circuit 56, and actuator 58, a temperature adjustor 60, a gas concentration adjustor 62 and a pressure apparatus 64 are provided. These are controlled by a controller 66 that is outside the incubator 52.

The culture unit 54 is a culture means for cultivating by imparting pressure and the previous described force F, etc. to the cell construct 2. Inside the culture unit 54, the culture chamber 36 that is the above described culture space is formed. The pressure apparatus 64 is controlled by the controller 66, and acts pressure P on a bottom face side of the culture bed 4 in the culture chamber 36.

The culture circuit 56 is a means for supplying and circulating the culture fluid 38, etc. to the culture means. The culture circuit 56 is constructed of a culture fluid tank 70 that stores the culture fluid 38, a gas exchanger 72 that supplies the mixed gas G (nitrogen, oxygen, carbon dioxide, etc.) to the culture fluid 38 and the culture room 53, a pump 74, a check valve 76 and a circulation tube 80 that connects the culture unit 54 to a pressure adjusting valve 78 adjusting pressure in the culture room 53 and the culture chamber 36.

For the pump 74, for example, a piston pump, a syringe pump and a peristaltic pump can be used. Drive of the pump 74, open and close of the pressure adjusting valve 78, a degree of open thereof, etc, are adjusted by the controller 66. The actuator 58 is a driving source for the culture unit 54 that imparts the force F to the cell construct 2. The temperature adjustor 60 adjusts temperature in the culture room 53 and the culture chamber 36. The gas concentration adjustor 62 adjusts concentration of the mixed gas G (nitrogen, oxygen, carbon dioxide, etc.) supplied to the culture fluid tank 70 and the culture fluid 38. The controller 66 controls each of the above function units. Concretely, the controller 60 may control all of temperature adjustment and gas concentration adjustment, etc., and may control circulation of the culture fluid tank 70, movement of the pump 74, movement of the actuator 58, etc.

By executing the above described cultivation process with such culture system 50, a cultivation process of loading bending motion can be executed, and the culture circuit 56 allows to supply the culture fluid 38 into the culture chamber 36 and exclude waste matters, etc. The pressure apparatus 64 can control pressure to the culture unit 54 continuously, intermittently or periodically, and cultivate a cell or tissue while temperature and pressure remains in a desired state. As a result, efficient and reliable cultivation can be executed.

In this culture system 50, the culture fluid tank 70, the actuator 58 and the pump 74 are provided inside the incubator 52. The culture system 50 is not limited to the above structure. All or a part thereof them may be structured outside the incubator 52. Concerning movement of the actuator 58, pressure to the culture chamber 36 in the pressure apparatus 64 and movement of the pump 74 supplying the culture fluid 38, etc. may be linked. If the cultivation process intermits in the middle thereof and bending motion is loaded periodically or intermittently, effective stimulation can be imparted to a cell.

Other Embodiment

In the above embodiments, to the cell construct 2 that is a culture, the force F is imparted from the back side of the culture bed 4, and by curving the culture bed 4 upwardly, the cell construct 2 is bent. A predetermined bending displacement may be imparted to the culture bed 4 or the cell construct 2 itself. In this process, the predetermined bending displacement may be imparted continuously or intermittently, or continuous or intermittent tension may be imparted periodically. In such structure, a predetermined vending can be also given to the cell construct 2.

Result of Experiment

A result of an experiment using the cultivating method of the present invention will be described with referring to FIGS. 14 and 18.

Figure 14:
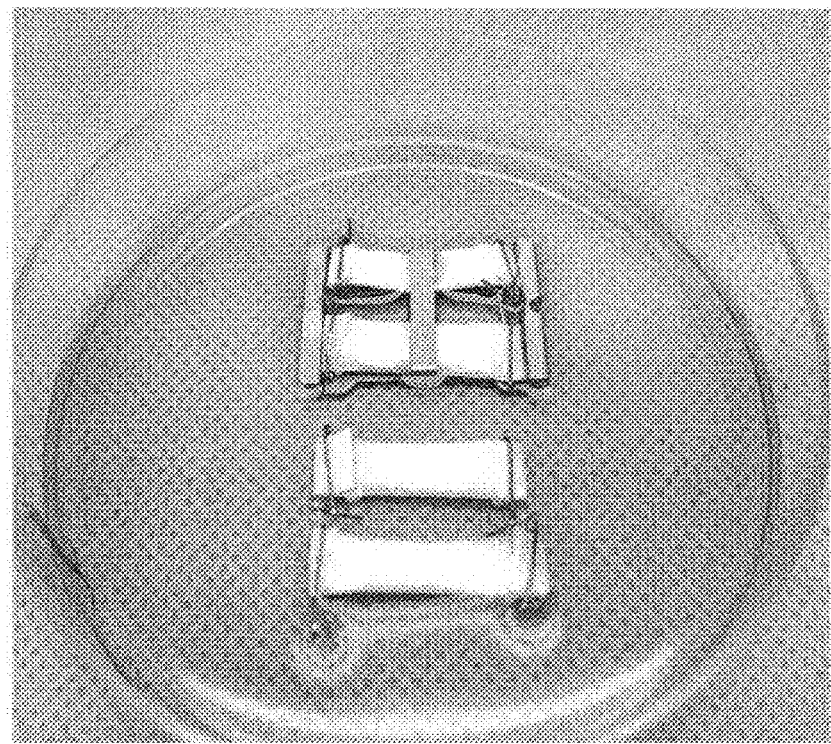
FIG. 14 depicts an experimental example.
Figure 15:
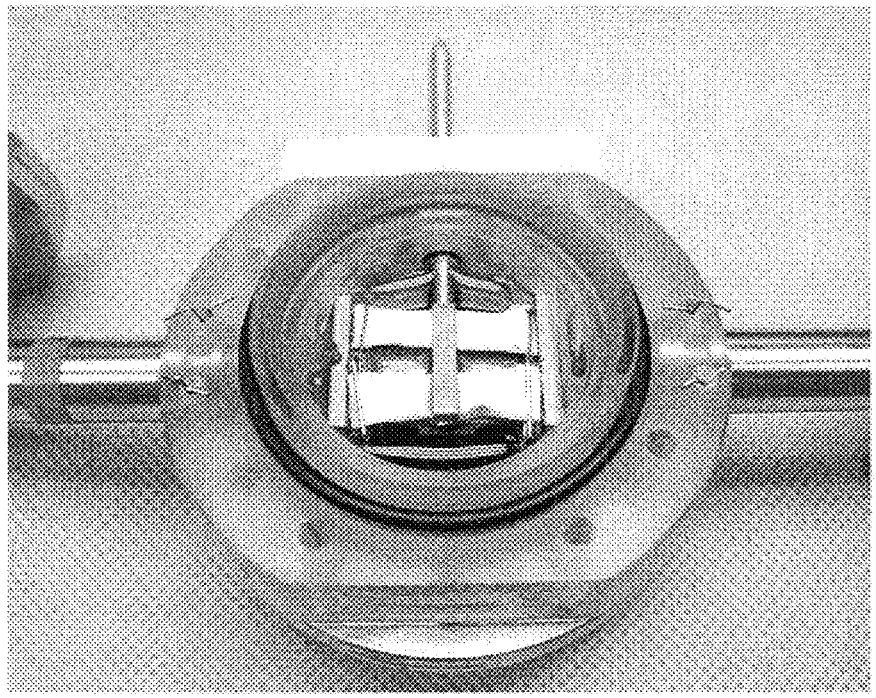
FIG. 15 depicts an experimental example.

FIG. 14 shows a cell construct. This cell construct is structured such that a cell suspended in a culture fluid is entered in a tube of a semi-permeable membrane. As shown in FIG. 15, the cell construct is fixed to a culture bed, and is accommodated in a culture chamber. In this case, a driving unit is separated from the culture chamber.

Pressure from an actuator acted on a culture unit, and bending motion is imparted to the cell construct. The actuator is disposed outside a culture room. A cable is penetrated through a door of the culture chamber to be connected to the driving unit. A movement state of the actuator could be confirmed by a display.

The actuator converts a rotating movement of a motor to straight line movement by a crank. By selection of the length of a crank arm, back and forth width of a wire could be adjusted, and in accordance with this, a size of bending imparted to the cell construct could be adjusted.

In this experiment, pressure movement is limited to bending motion, atmospheric pressure is maintained and the culture fluid is circulated. Pressure and bending motion by the actuator are imparted individually, irrelevantly and solely. In the experiment, for example, it can be considered that pressure equal to or over 0.5 (MPa) is imparted.

Figure 16:
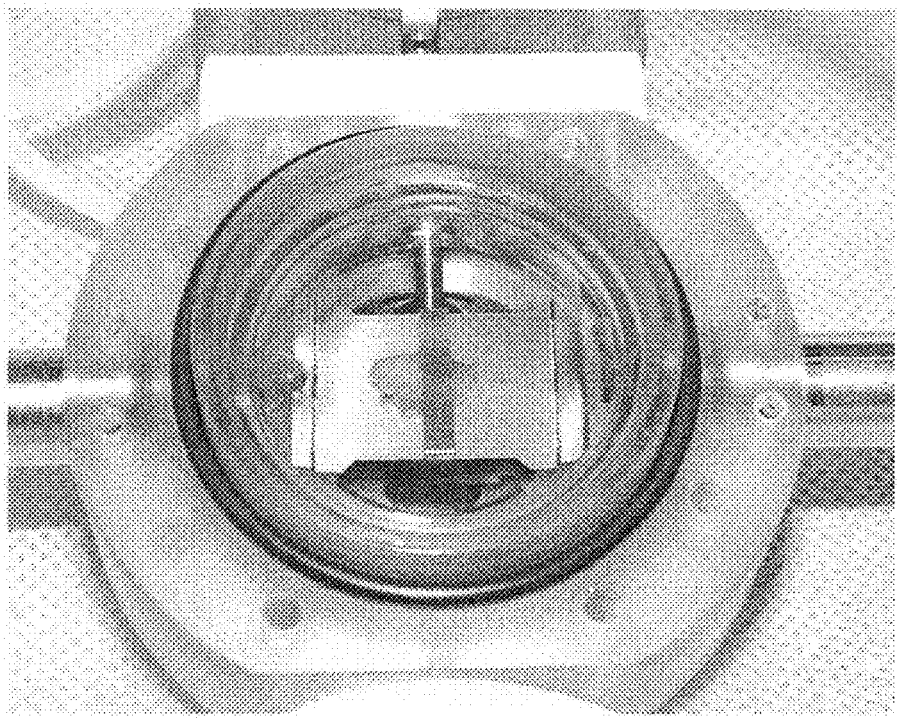
FIG. 16 depicts an experimental example.
Figure 17:
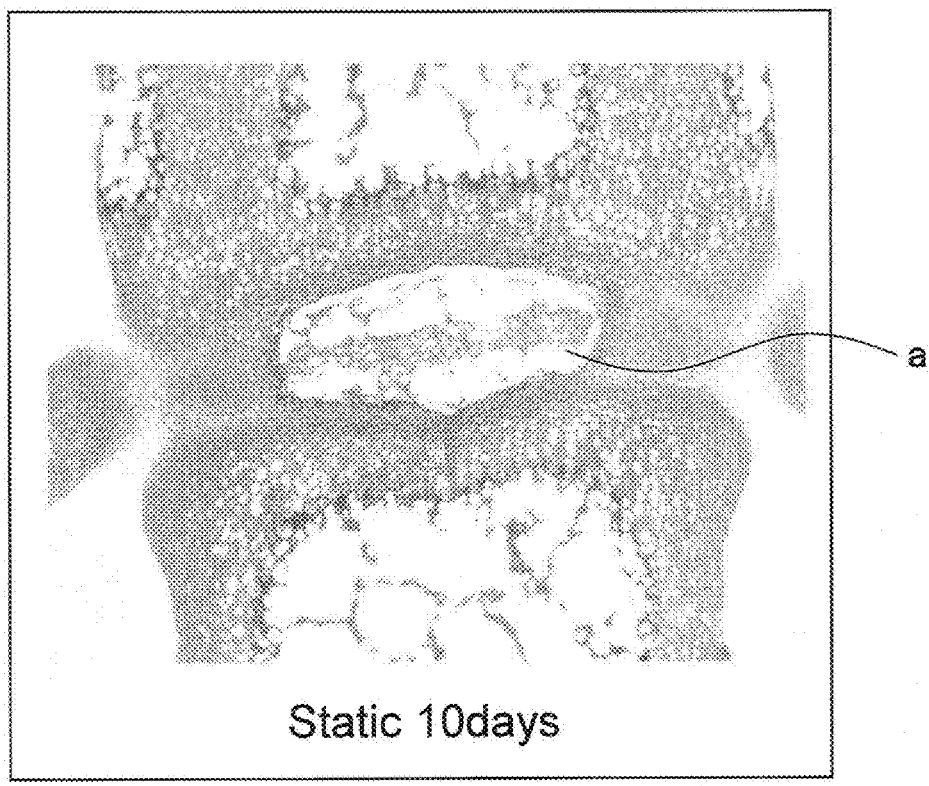
FIG. 17 depicts an experimental example.
Figure 18:
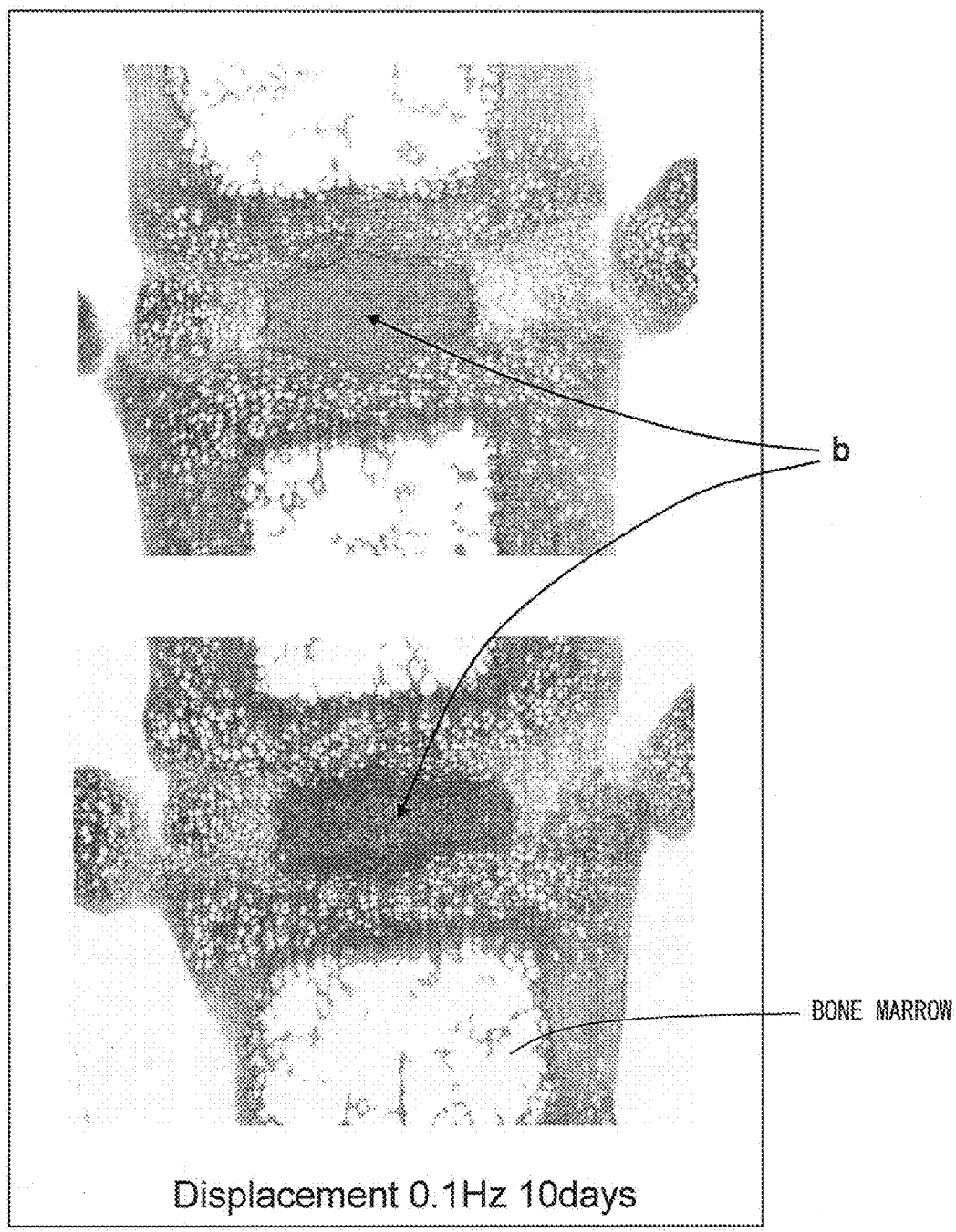
FIG. 18 depicts an experimental example.

FIGS. 16 to 18 show an experiment of vertebrae organ culture of a two days old mouse. In the experiment, a vertebra taken out from the two days old mouse is disposed on the culture bed (FIG. 16) and bending motion of 0.1 (Hz) frequencies is imparted to be cultivated for ten days. In this experiment, no pressure is applied.

As a comparison example, static cultivation is executed. FIGS. 17 and 18 show static cultivation for ten days. After ten days, a section of an organ is toluidine blue-stained, and condition of a cell existing is observed. In FIGS., a stained part can not be expressed. A part where brightness falls down (showing a stained part) shows existence of a living cell. In the static cultivation, cell density inside discs does not rise, and displacement of matrixes can be seen (a of FIG. 17).

On the contrary, in vertebrae where bending motion and displacement are imparted, growth of cells and store of neogenetic matrixes can be seen inside discs. (b of FIG. 18).

From the result of the experiment, in the cultivation of imparting bending motion, growth of cells and store of neogenetic matrixes could be seen as compared with the static cultivation. Thus, it can be guessed that bending motion thereof gives stimulation to the cell construct, and substance migration is promoted.

While the present invention has been described with the preferred embodiments, the description is not intended to limit the present invention. Various modifications of the embodiments based on the subject matters and objects described in claims or disclosed in this specification will be apparent to those skilled in the techniques, and such modifications rightfully fall within the true scope of the present invention.

The present invention relates to a method for cultivating of a cell or tissue. Stimulation by bending motion is given to a cell construct, and substance migration in neogenetic tissue without a blood vessel is promoted to promote propagation of cells, and cultivation in a state where tissue in vivo is imitated can be executed. So, the present invention is useful.

What is claimed is:

1. A cultivating method of a culture including a cell and/or tissue, comprising:
    putting the culture including the cell, the tissue or both thereof into a tube made from a semi-permeable membrane, through which a culture fluid can pass, and sealing the tube;
    disposing a culture bed in a culture chamber which stores the culture fluid and in which the culture fluid is circulated, disposing the tube on a disposing part of the culture bed, the disposing part having elasticity so as to be curved by a load and be restored to its original form by cancellation of the load, and inserting the tube into each through hole in standing walls to hold the tube on the disposing part, the standing walls facing each other with the disposing part therebetween;
    curving the disposing part by imparting the load to a back side of the culture bed to apply bending motion to the culture in the tube;
    restoring the disposing part to its original form by canceling the load from the back side to apply the bending motion to the culture in the tube in a direction where the disposing part is restored; and
    repeating the steps of said curving and restoring at least once, wherein the bending motion is applied to the culture in the tube periodically by restoration movement of the culture bed which results from the load to the culture bed and the cancellation of the load, and the culture fluid is supplied to the culture in the tube.

2. The culture method according to claim 1, wherein the bending motion includes a process that brings the culture into a curving state.

3. The culture method according to claim 1, wherein the bending motion is executed by the medium of the culture bed.

4. The culture method according to claim 1, wherein the culture bed at its both ends is movably held, and the culture bed is curved by imparting the load to a center part of the culture bed.

5. The culture method according to claim 1, wherein the bending motion is executed periodically or intermittently.

6. The culture method according to claim 1, wherein the culture includes any of the cell, a cell scaffold, and an extracellular matrix produced by the cell.

7. The culture method according to claim 1, wherein the culture is a three-dimensional culture scaffold where the cell is disseminated.

8. The culture method according to claim 1, wherein the culture includes a gel substance.

9. The culture method according to claim 7, wherein the three-dimensional culture scaffold is a bioabsorbable material.

10. The culture method according to claim 8, wherein the gel substance is a bioabsorbable material.

11. The culture method according to claim 1, wherein the bending motion is generated for the culture by any of
    imparting continuous force to the culture, imparting intermittent force to the culture, or imparting continuous or intermittent force to the culture periodically.

12. The culture method according to claim 1, further comprising pressuring the culture by pressuring the culture chamber, wherein pressure to the culture is given continuously or intermittently, or is changed periodically or irregularly.

13. The culture method according to claim 1, wherein the bending motion is generated by imparting continuous force to the culture.

14. The culture method according to claim 1, wherein the bending motion is generated by imparting intermittent force to the culture.

* * * * *

UNITED STATES PATENT AND TRADEMARK OFFICE
CERTIFICATE OF CORRECTION

| | |
|---|---|
| PATENT NO. | : 8,431,401 B2 |
| APPLICATION NO. | : 12/307978 |
| DATED | : April 30, 2013 |
| INVENTOR(S) | : Setsuo Watanabe et al. |

It is certified that error appears in the above-identified patent and that said Letters Patent is hereby corrected as shown below:

On the title page item (75), the city of residence of inventor Watanabe should be "Fuji-shi," not "Fuji."

Signed and Sealed this
Twenty-fifth Day of June, 2013

Teresa Stanek Rea
*Acting Director of the United States Patent and Trademark Office*